US007316332B2

(12) United States Patent
Powers et al.

(10) Patent No.: US 7,316,332 B2
(45) Date of Patent: Jan. 8, 2008

(54) WEARABLE SKIN TREATMENT DEVICE

(76) Inventors: Jeffrey Lewis Powers, 50114 E. Fellows Creek Ct., Plymouth, MI (US) 48170; Dennis Willard Davis, 427 E. Washington Ave., Eustis, FL (US) 32726; David Paul Thimm, 48770 Quail Run Dr., SW., Plymouth, MI (US) 48170; James Marvin Stenz, 7090 Linden Rd., Fenton, MI (US) 48430

( * ) Notice: Subject to any disclaimer, the term of this patent is extended or adjusted under 35 U.S.C. 154(b) by 0 days.

(21) Appl. No.: 10/915,720

(22) Filed: Aug. 10, 2004

(65) Prior Publication Data
US 2005/0124945 A1 Jun. 9, 2005

Related U.S. Application Data

(63) Continuation-in-part of application No. 10/729,757, filed on Dec. 5, 2005, now Pat. No. 7,135,011, which is a continuation-in-part of application No. 10/314,825, filed on Dec. 9, 2002, now abandoned.

(60) Provisional application No. 60/515,718, filed on Oct. 30, 2003, provisional application No. 60/515,775, filed on Oct. 30, 2003, provisional application No. 60/515,793, filed on Oct. 30, 2003, provisional application No. 60/515,794, filed on Oct. 30, 2003.

(51) Int. Cl.
B67D 5/64 (2006.01)
(52) U.S. Cl. ............... 222/175; 222/1; 222/192; 222/212; 222/213; 222/490; 222/491; 222/494; 224/148.6; 604/310

(58) Field of Classification Search ............ 222/185, 222/175, 78–79, 212, 148.1, 148.4, 148.6, 222/192, 206, 494, 213–215, 1, 490–491; 604/309–311, 289; 224/148.1, 148.4, 148.6, 224/148.2
See application file for complete search history.

(56) References Cited

U.S. PATENT DOCUMENTS

| | | | | |
|---|---|---|---|---|
| 692,089 | A * | 1/1902 | Swisher | 224/148.7 |
| 2,235,350 | A * | 3/1941 | Anderson | 224/148.7 |
| 3,845,770 | A * | 11/1974 | Theeuwes et al. | 424/427 |
| 4,058,237 | A * | 11/1977 | Luke | 222/78 |
| 4,176,772 | A * | 12/1979 | Danon | 224/148.5 |
| 4,241,850 | A * | 12/1980 | Speer et al. | 222/39 |
| 4,550,861 | A * | 11/1985 | Fay et al. | 222/78 |
| 4,728,006 | A * | 3/1988 | Drobish et al. | 222/181.3 |
| 4,739,906 | A * | 4/1988 | LoTurco | 222/212 |
| 4,932,566 | A * | 6/1990 | Weinbaum | 222/175 |
| 4,988,097 | A * | 1/1991 | Smith et al. | 482/105 |
| 4,991,745 | A * | 2/1991 | Brown | 222/212 |
| D315,245 | S * | 3/1991 | Envall | D3/202 |
| 5,072,935 | A * | 12/1991 | McWain | 482/105 |
| D323,430 | S * | 1/1992 | Niederkorn | D3/202 |
| 5,088,624 | A * | 2/1992 | Hackett et al. | 222/78 |
| 5,169,030 | A * | 12/1992 | Lewin | 222/92 |
| 5,186,347 | A | 2/1993 | Freeman et al. | |
| 5,339,995 | A * | 8/1994 | Brown et al. | 222/173 |

(Continued)

*Primary Examiner*—Frederick C. Nicolas

(57) ABSTRACT

Persons often encounter the need to apply some form of skin treatment when on the go. Such treatments include disinfectant, sunscreens, medications, and moisturizing lotions. The present invention comprises convenient portable skin treatment dispensers in the form of neck-worn and disposable wrist-worn devices. The devices are convenient to use, unobtrusive and can even be disposable. Ease of manufacture is facilitated in various embodiments which include self-sealing diaphragm valves.

6 Claims, 50 Drawing Sheets

U.S. PATENT DOCUMENTS

| | | | |
|---|---|---|---|
| 5,358,144 A * | 10/1994 | Mock | 222/78 |
| 5,409,144 A * | 4/1995 | Brown | 222/185.1 |
| 5,484,085 A * | 1/1996 | Bennett | 222/175 |
| 5,538,164 A * | 7/1996 | Rivas | 222/153.04 |
| 5,655,687 A | 8/1997 | Fitten et al. | |
| 5,667,107 A * | 9/1997 | Lindsey | 222/173 |
| 5,678,730 A * | 10/1997 | Fabek et al. | 222/78 |
| D408,988 S * | 5/1999 | Barber et al. | D3/215 |
| 5,924,601 A * | 7/1999 | Chen | 222/175 |
| 5,927,548 A * | 7/1999 | Villaveces | 222/82 |
| 5,957,347 A * | 9/1999 | White et al. | 224/148.1 |
| 6,053,364 A | 4/2000 | van der Heijden | |
| 6,126,041 A * | 10/2000 | DiTomasso et al. | 222/95 |
| 6,173,866 B1 * | 1/2001 | Taylor et al. | 222/175 |
| 6,228,375 B1 * | 5/2001 | Kocher | 424/400 |
| 6,234,357 B1 * | 5/2001 | Lewis | 222/175 |
| 6,415,960 B1 * | 7/2002 | Fink et al. | 222/175 |
| 6,540,106 B2 * | 4/2003 | Gerstner | 222/78 |
| 6,581,811 B1 * | 6/2003 | Schillaci | 224/148.2 |
| 7,004,354 B2 * | 2/2006 | Harper | 222/94 |
| 7,135,011 B2 * | 11/2006 | Powers et al. | 604/310 |
| 2001/0042758 A1 * | 11/2001 | DiTomasso et al. | 222/95 |

* cited by examiner

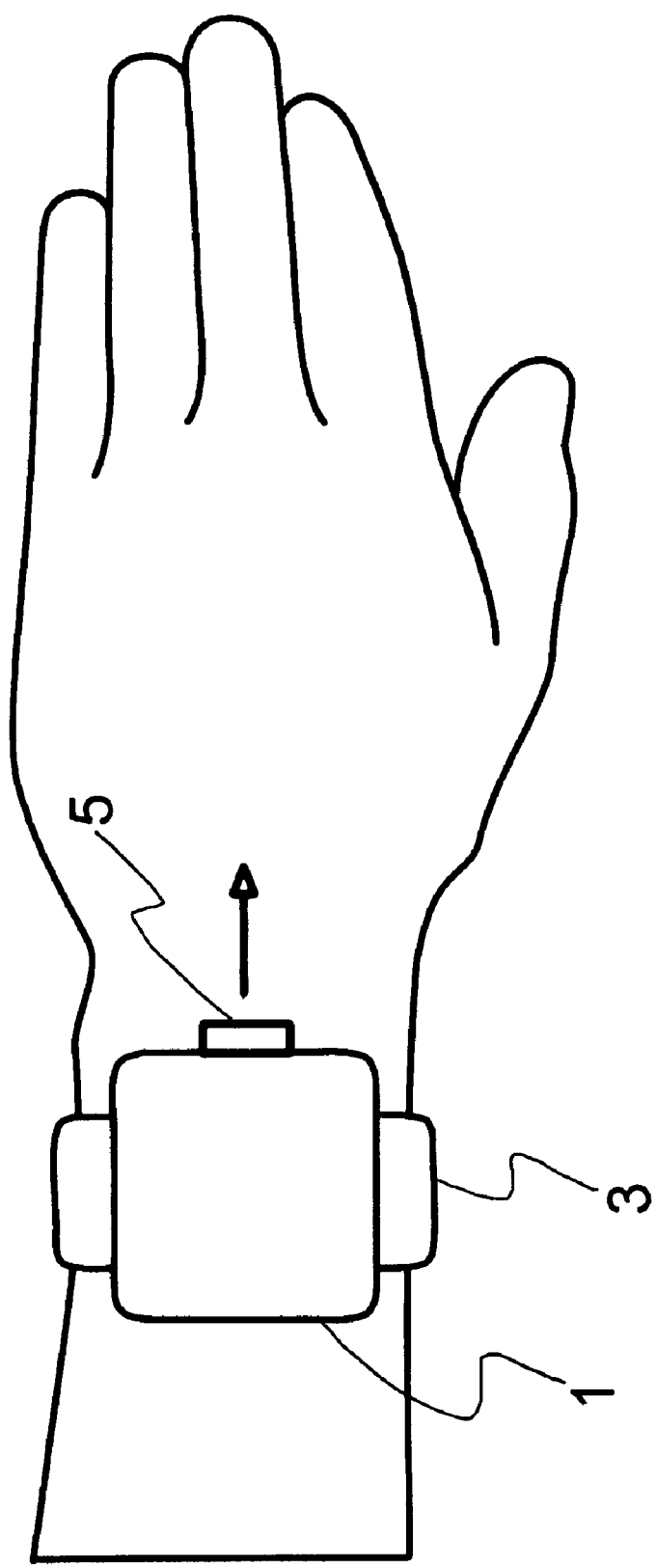

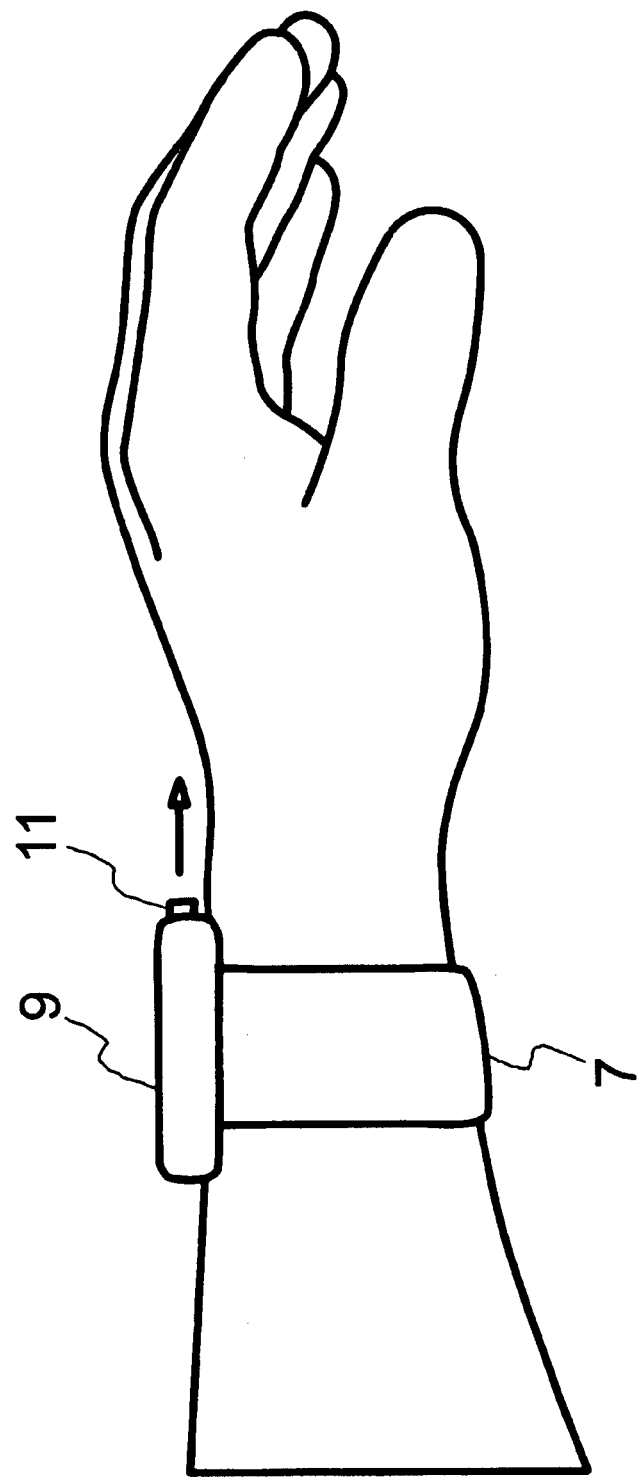

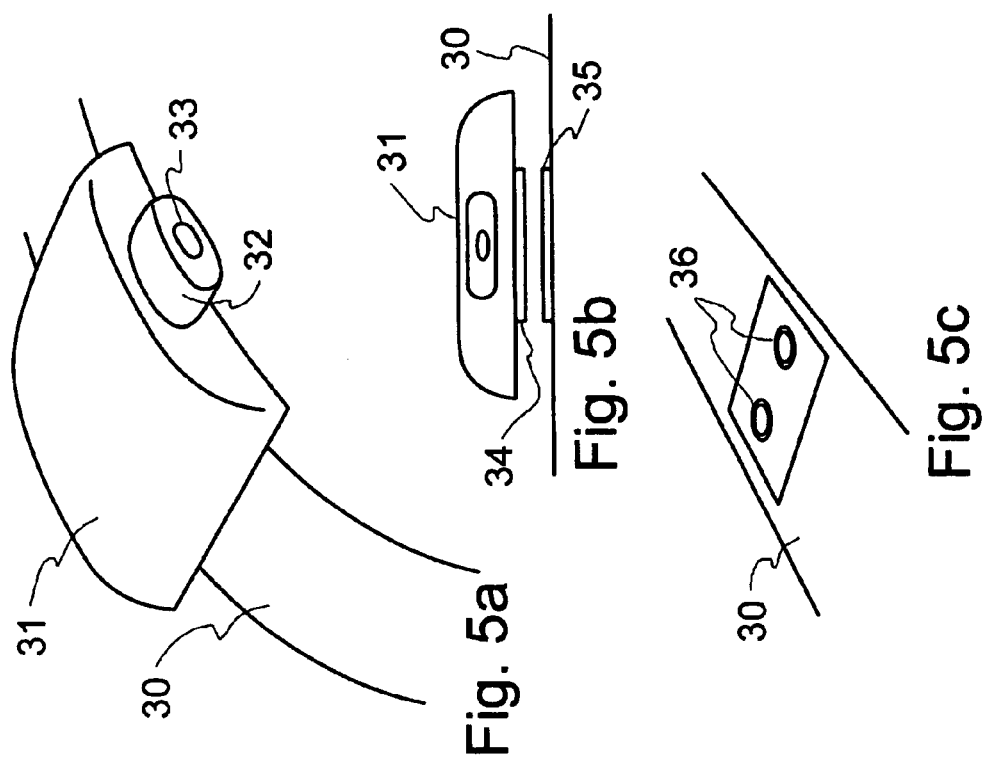

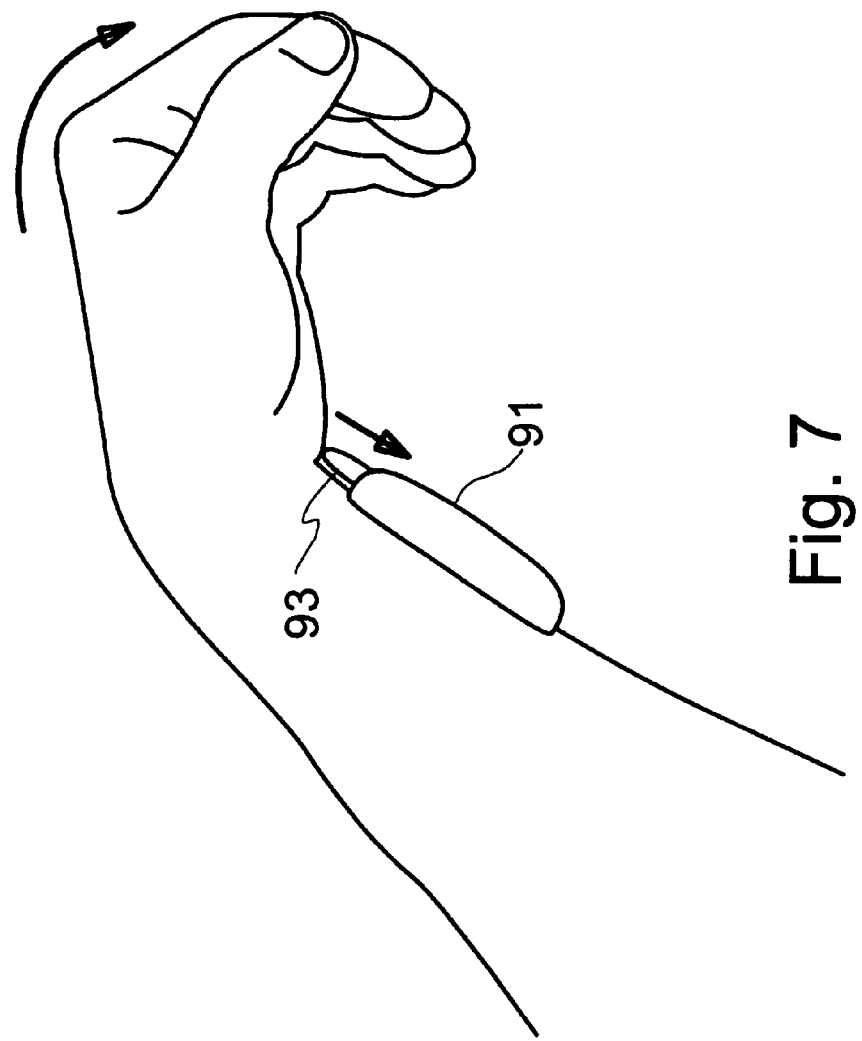

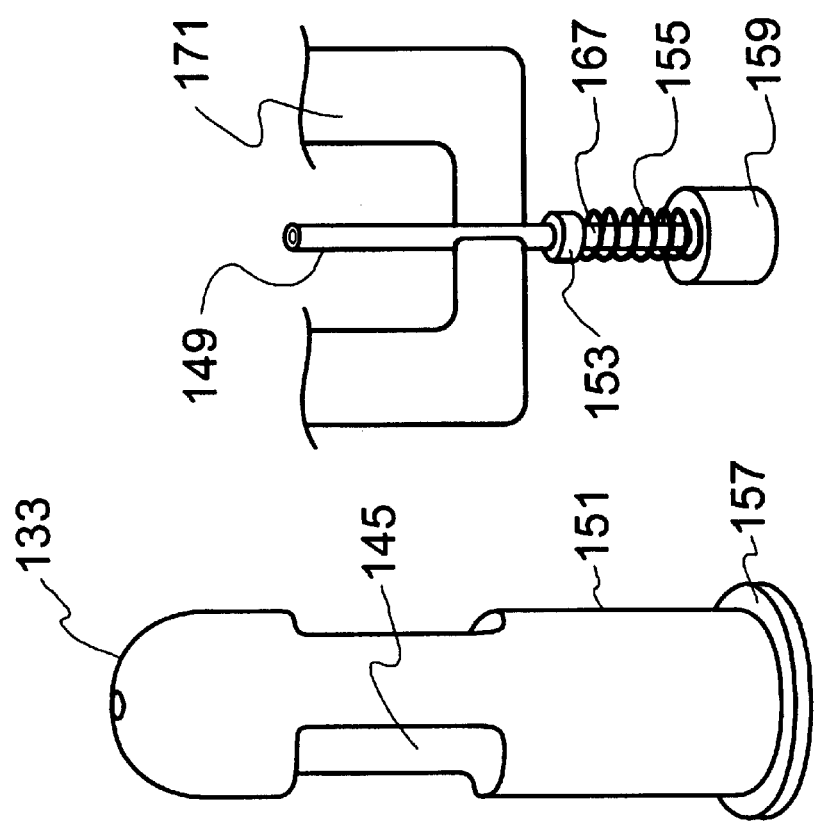

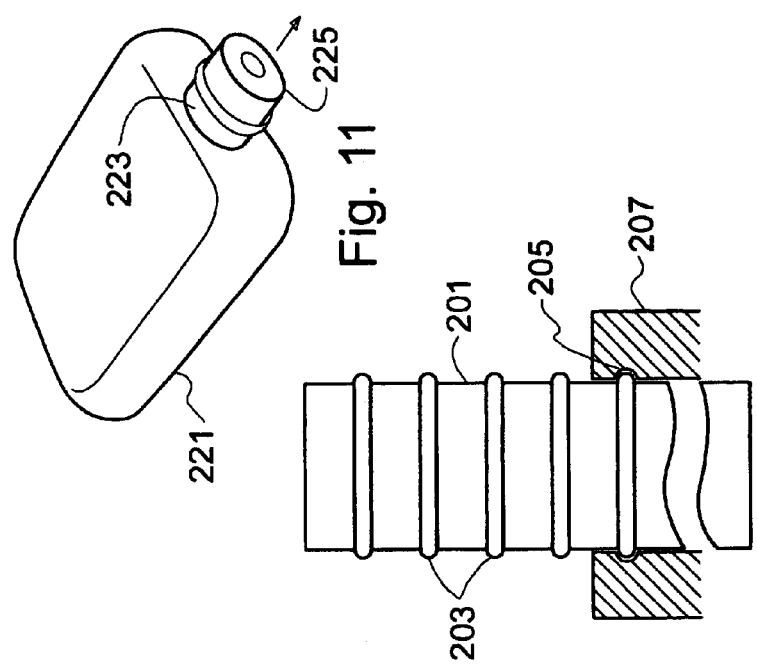

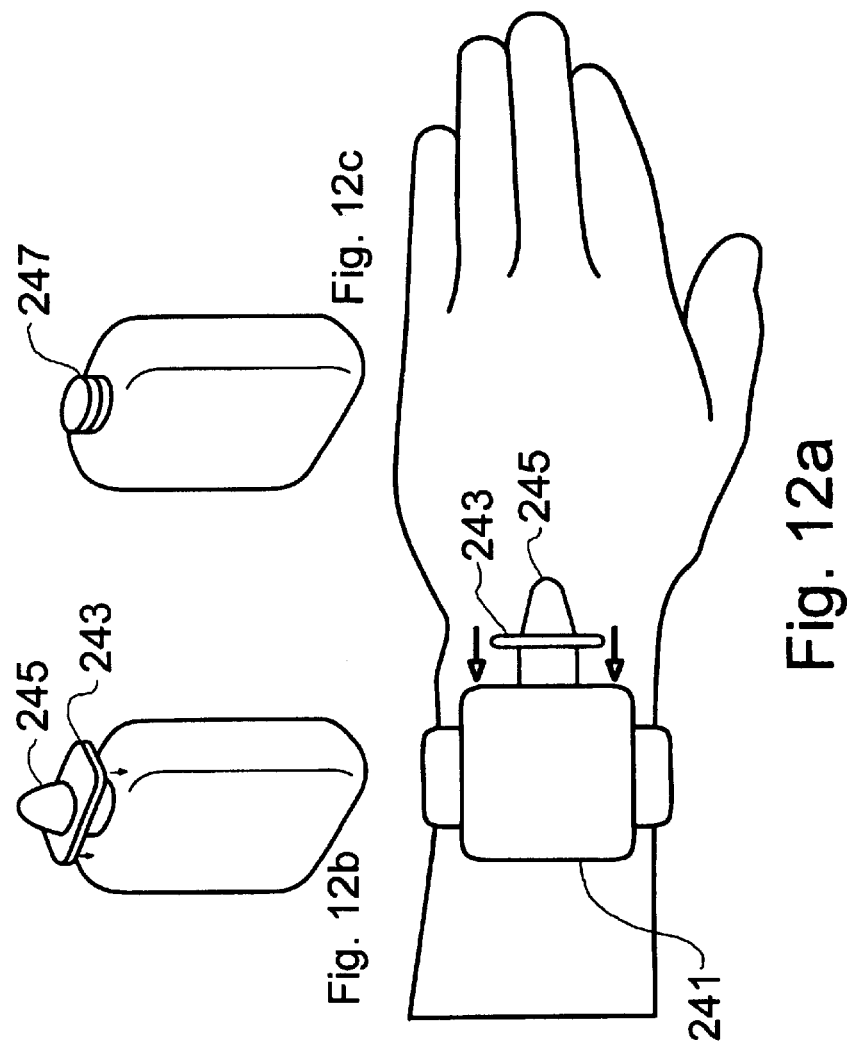

Clear windows allow user to see remaining sanitizer

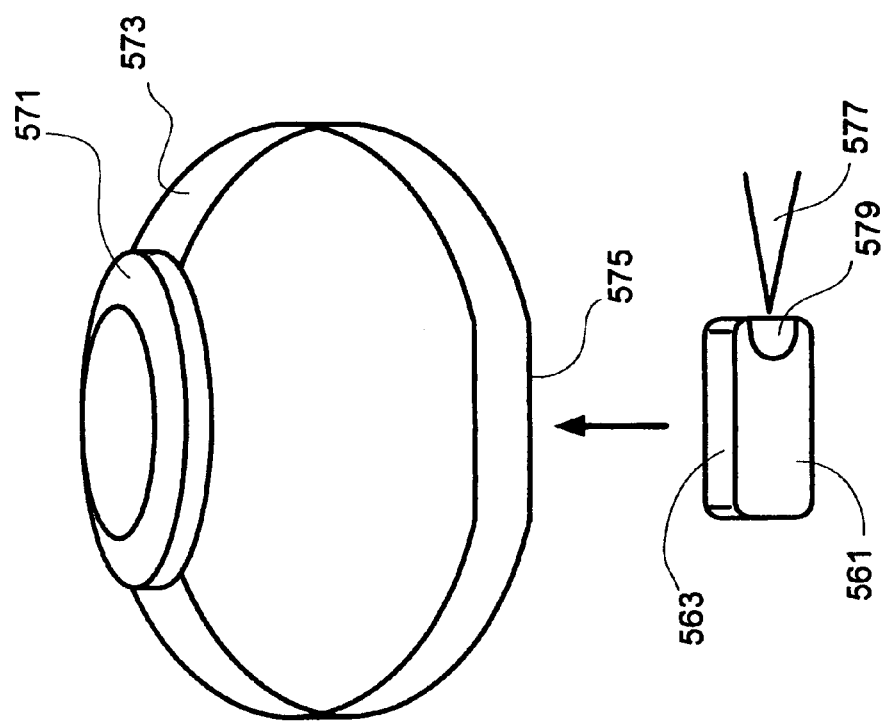

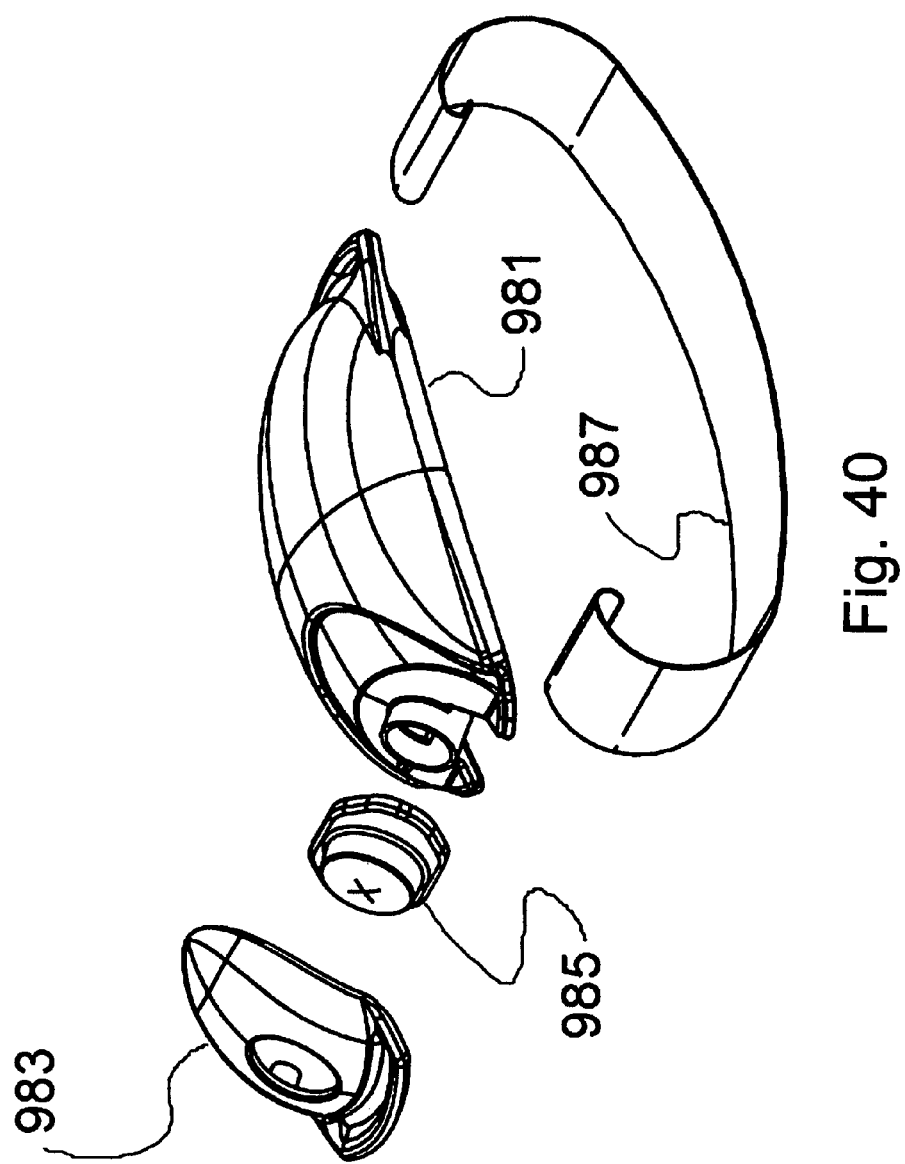

WEARABLE SKIN TREATMENT DEVICE

REFERENCE TO RELATED APPLICATION

This application is a continuation-in-part of application Ser. No. 10/729,757, filed Dec. 5, 2003 now U.S. Pat. No. 7,135,011 which is a continuation-in-part of application Ser. No. 10/314,825, filed Dec. 9, 2002, now abandoned. This application claims the benefit of U.S. Provisional Application Nos. 60/515,718, 60/515,775, 60/515,793, and 60/515,794 filed Oct. 30, 2003, Disclosure Document No. 525,532, filed Feb. 5, 2003, Disclosure Document No. 534,422, filed Jul. 7, 2003, and Disclosure Document No. 536,414, filed Aug. 8, 2003.

BACKGROUND-PRIOR ART

The increase in bacterial immunity to modern antibiotics is problematic and one of the chief vectors of infection is the human hand. Hence, when not in the proximity of a washroom to disinfect one's hands, it would be useful to have a means to accomplish such sanitation. Also, in the midst of daily activities, it can be inconvenient to uncap bottles of disinfecting gels or hand lotions to otherwise treat the hands.

Fortunately, it has been established that ethyl alcohol is a most effective antiseptic for gram-negative pathogens; it is of low viscosity, easily dispensed from a portable container, and does not require the use of a material wipe or cloth because of the speed of evaporation. Further, an adequate dose for sanitizing the hands comprises but a few drops of this antiseptic. To prevent chafing, glycerin can be added to the alcohol without levels of viscosity increase that would be deleterious to the dispensing process.

Various methods of portable disinfectant or lotion dispensers have been disclosed in the prior art. These include body-mounted dispensers, wrist bracelet dispensers, and others. U.S. Pat. No. 6,371,946 discloses a dispensing tube that drips liquid onto the hand. U.S. Pat. No. 6,053,898 discloses a tube-fed finger dispenser. A body-worn dispenser of form factor similar to a pager is disclosed in U.S. Pat. No. 5,927,548.

What has not been demonstrated is a dispenser that is wrist- or arm-worn that provides ease of actuation and, more specifically, single hand actuation. Neither has there been a device that can be surreptitiously actuated. This is an important consideration with respect to public relations. Individuals such as business and sales personnel may come in contact with and greet many people during the day. It would be desirable to have the option of sanitizing the hands after a handshake with a person without conveying a disdainful message to that person in so doing.

A wrist-mounted or neck-worn dispenser that achieves dispensing directly to the hand with a simple hand action is a major advantage of the present invention. This is especially useful to nurses and doctors in busy hospital settings, as well as for allied health care workers who cannot take time to repeatedly wash their hands with soap and water.

SUMMARY OF THE INVENTION

The present invention discloses a wrist- or forearm-mounted device and neck-worn versions for dispensing a small amount of alcohol-based disinfectant hand rub, moisturizer, or other skin medicament. Even powder-based skin treatments can be dispensed using the present invention. A wristband or other attachment means affix the device to arm or wrist. Various locations are feasible including the top, side, or underside of the wrist or forearm. One embodiment provides for a finger-mounted geometry. In a preferred embodiment, the device is in the form of a low profile, wrist-mounted dispenser with a nozzle that produces a small amount of dispensed skin treatment when actuated. In an another preferred embodiment, a compact version of the dispenser can be worn about the neck on a lanyard or necklace.

Surreptitious actuation and dispensing of hand treatments is made possible with embodiments of the invention that are mounted on the underside of the wrist and can be easily actuated in a causal, not easily detected manner.

Because only a few drops of alcohol-based disinfectant comprise a dose adequate to achieve sanitation of the hands, the device can dispense hundreds of doses of disinfectant before requiring refill or disposal. It can be used at any orientation of the arm and will avoid leakage when not actuated. Options exist for the fabrication of the device whether disposable or refillable. For example, hard or soft pliable plastics can be employed. For disposable versions of the device, biodegradable plastics are cited as advantageous device construction materials. Various embodiments of the invention include different mechanical designs for actuation, dispensers detachable from wristbands, cartridge-based dispensers, dispensers with functioning watch faces, hybrid watch-dispensers, and methods of mounting to the top, side, or underside of the wrist or arm along with corresponding nozzle designs.

OBJECTS AND ADVANTAGES

Several objects and advantages of the present invention are:
(a) Provide a convenient, portable means for dispensing skin treatments;
(b) Provide a cost-effective means for dispensing skin treatments;
(c) Provide an unobtrusive means of dispensing skin treatments;
(d) Provide an easily actuated means of dispensing skin treatments:
(e) Provide an arm- or wrist-mounted means of dispensing skin treatments;
(f) Provide a wrist-mounted disposable means of dispensing skin treatments;
(f) Provide a cartridge- or packet-based means of dispensing skin treatments;
(g) Provide a skin treatment dispenser with wristwatch functionality.
(h) Provide a neck-worn skin treatment dispenser.
(h) Provide a disposable wrist-worn skin treatment dispenser.
(h) Provide an easy-to-manufacture skin treatment dispenser using a diaphragm valve.

BRIEF DESCRIPTION OF THE DRAWINGS

FIG. 1a is a pictorial diagram of the basic form of a dispenser mounted on the top side of the wrist.

FIG. 1b is a pictorial diagram of articulation of the hand to receive hand treatment dispensed from the device of FIG. 1a.

FIG. 5*a* is a pictorial diagram of dispenser detachable from a wristband.

FIG. 5*b* is an end view of a dispenser of FIG. 5*a* attachable to a wristband using Velcro.

FIG. 5*c* is a pictorial view of snaps used to attach a dispenser of FIG. 5*a* to a wristband.

FIG. 7 is a pictorial view of the wrist motion actuation of a plunger-based dispenser.

FIG. 9*b* is a pictorial view of components of the pressure-multiplying plunger dispenser.

FIG. 10 is a cross-sectional view of an adjustable nozzle.

FIG. 11 is a pictorial view of a dispenser with a flow adjusting nozzle.

FIG. 12*a* is a pictorial view of a detachable plunger-based dispenser with the plunger collinear with the fluid ejection axis.

FIG. 12*b* is a perspective view of the dispenser of FIG. 12*a*.

FIG. 12*c* is a pictorial view of the a dispenser having a cap.

FIG. 27 is a pictorial diagram of a dispenser removably attachable to a wristwatch band.

FIG. 40 is an exploded diagram of a slit-based membrane valve embodiment of the invention in which the valve is captivated by a retainer.

Figure 2:
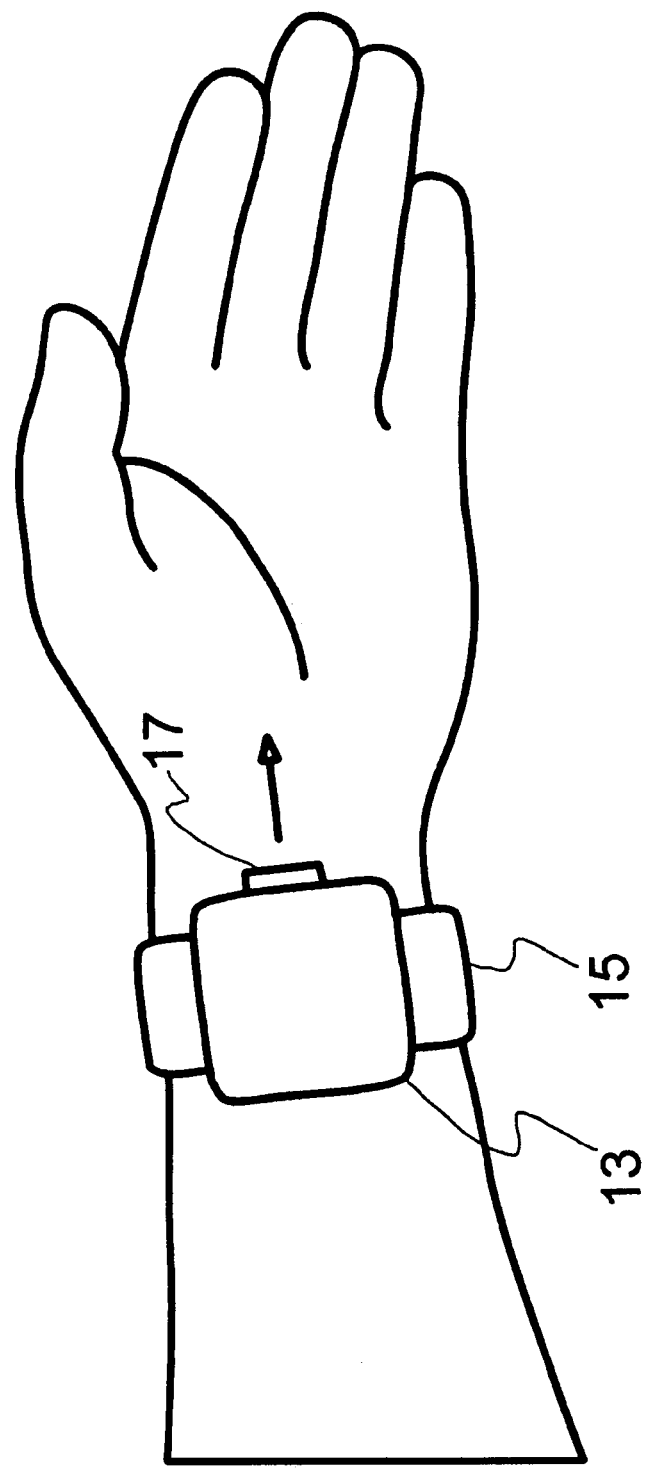
FIG. 2 is a pictorial diagram of the basic form of a dispenser mounted on the under side of the wrist.

The following definitions serve to clarify the disclosed and claimed invention:

Bladder refers to an elastic, resilient container that can be deformed under compression.

Pressure-multiplying refers to those devices relying on the technique of increasing, by mechanical advantage, the compression pressure of a working fluid. This is achieved by use of an ejection fluid-containing tube that penetrates an ejection fluid-containing piston under the influence of the working fluid.

Skin treatment material comprises any of a host of liquid, powder, gel, or aerosol medications, or sanitizing agents that are topically applied to the hands or other skin surfaces. Examples include alcohol, glycerin, moisturizing lotions, sunscreen, and desiccating powders. The combination of treatments such as disinfecting lotion and sunscreen are included in this definition.

Working fluid refers to the fluid which transfers manual pressure to the material to be dispensed. Such transfer of pressure can occur in one or multiple stages and typical working fluids include air contained in a squeeze bottle as well as liquid versions of the hand treatment material itself.

Diaphragm valve refers to a membrane having one or more slits that form flaps in the membrane. These flaps are normally closed but can be caused to open upon fluid or gas pressure applied to one side of the membrane. In this way, the diaphragm valve mimics the operation of human heart valves such as the tricuspid valve.

DETAILED DESCRIPTION OF THE INVENTION

The present invention is useful for dispensing either hand treatments such as moisturizers or disinfectants; even powders can be dispensed in powder-aerosol form. Typically, the active ingredient in hand antiseptics such as Purel is ethyl alcohol. This is fortuitous because it is a relatively non-toxic liquid that exhibits low viscosity over the temperature range of interest for this application. This makes delivery of a directed stream of fluid relatively easy. In contrast to liquid, alcohol gels are useful in that they do not run and although they will require more force to dispense than liquid, such higher viscosity disinfectant or moisturizing formulations can be accommodated in differing embodiments of the present invention. Various means of dispensing the aforementioned hand treatments are feasible and can be tailored to the type of material to be dispensed. The target locations for deposition of the hand treatment include the regions on the top of the hand, and the underside of the hand, either fingers or palm. The preferred embodiment for a means of dispensing hand cleaning dosages in a device that attaches to either the top or underside of the wrist. It can be worn unobtrusively underneath a long-sleeved shirt.

Various approaches can be used to create the fluid dispenser. In a simple squeeze compartment design, a bladder reservoir expels fluid upon application to the bladder itself. In a plunger-based design, a syringe-type plunger causes the fluid in a reservoir to be expelled upon application of force to the plunger. Spray or squirting mechanisms analogous to squirt guns use a more specialized plunger mechanism and include a nozzle. A drip system would rely on gravity feeding of the liquid through some orifice for delivery to the hand. More elaborate schemes include use of a prime mover such as a miniature electrical actuator or pump.

Following is a taxonomy of dispenser types identified:
Squeeze
simple compression
pressure-multiplied compression
Plunger
simple plunger
pressure-multiplied plunger
same hand-actuated
Drip
Gas Pressurized
disposable
gas cartridge
Pump
thermoelectrically-heated working fluid
electromechanical
Remote Control—Low Power Radiofrequency, Single Chip Receiver

Basic Configuration

There are two fundamental approaches to dispensing hand treatment. In one approach, the hand treatment is dispensed to the hand of the arm upon which the dispenser is mounted. Actuation of this dispenser can be by either hand. In the second approach, the hand treatment is dispensed to the hand of the arm which does not have a dispenser attached. In this case, it is also true that actuation of the dispenser can be by either hand. The various embodiments discussed below will use one of these two approaches. Typically, hand treatment material will be ejected either parallel or perpendicular to the longitudinal axis of the forearm. In a preferred embodiment that uses the second aforementioned approach, the hand treatment material is ejected perpendicular to the longitudinal axis of the arm upon which the dispenser is mounted.

The simplest reduction to practice would be a low profile bladder, with associated orifice or nozzle for ejection of hand treatment, mounted on the wrist. FIG. 1a depicts a hand treatment dispenser 1 having an aperture or nozzle 5 for dispensing hand treatment material to a surface of the hand. It is shown mounted to the top side of the wrist by means of a strap 3. The dispenser is characteristically actuated by compression of the bladder comprising the dispenser. Details of its construction and various embodiments are discussed below. FIG. 1b depicts the slight upward articulation of the hand about the wrist that is conducive to dispensing treatment from nozzle 11 to the top of the hand upon compression of dispenser 9 attached to wristband 7. FIG. 2 depicts the dispenser 13 mounted by strap 15 to the underside of the wrist for dispensing of treatment to the palm of the user's hand by way of nozzle 17. Mounting to the underside of the wrist provides a more covert implementation, especially if worn under a long-sleeved shirt or blouse.

The dispenser can be removably attached to the wrist band so the user can mount it to the top, side, or bottom of the wrist to suit the user's desire. Various attachment schemes including Velcro, snaps, and other methods, as well as various nozzle configurations that are compatible with these various mounting schemes are discussed in detail below.

Figure 3A:
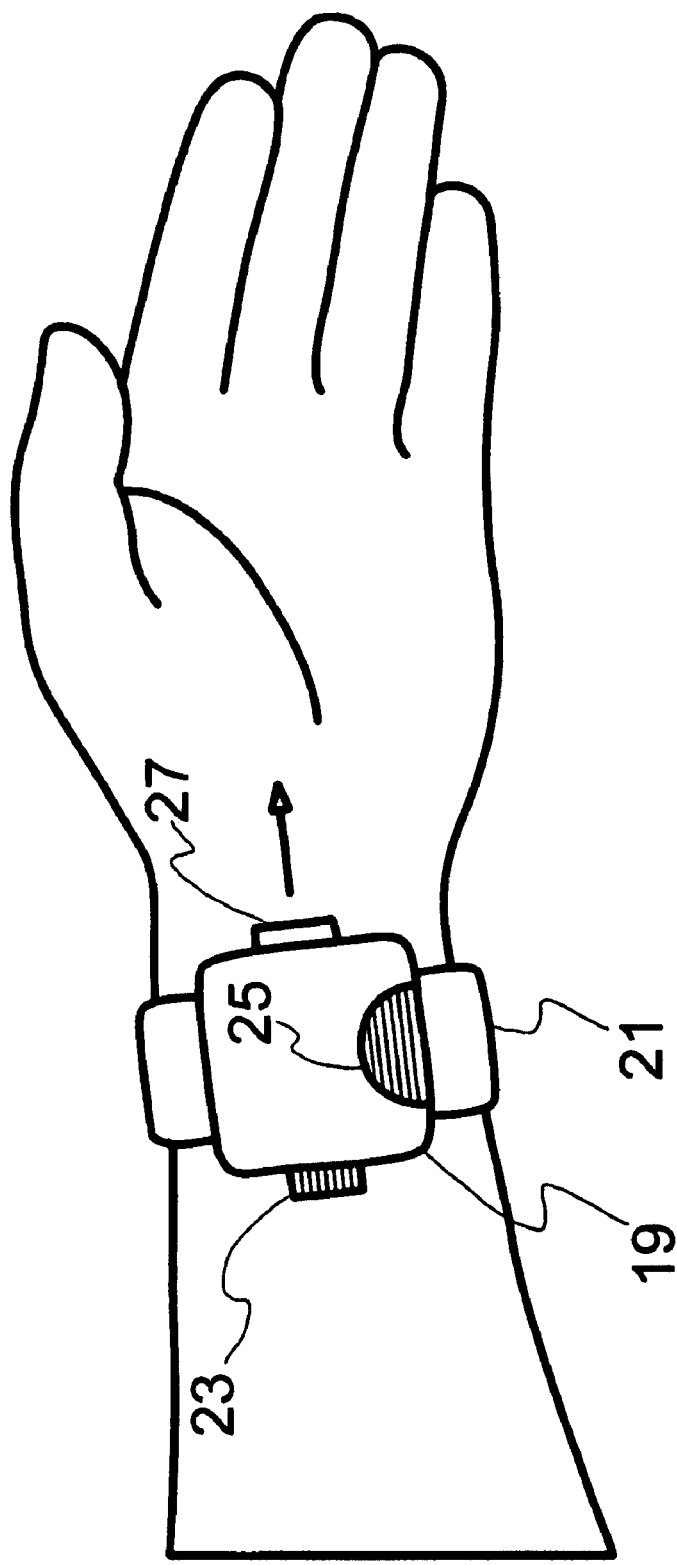
FIG. 3a is a pictorial diagram of a dispenser exhibiting a refill port and actuation area mounted on the under side of the wrist.
Figure 3B:
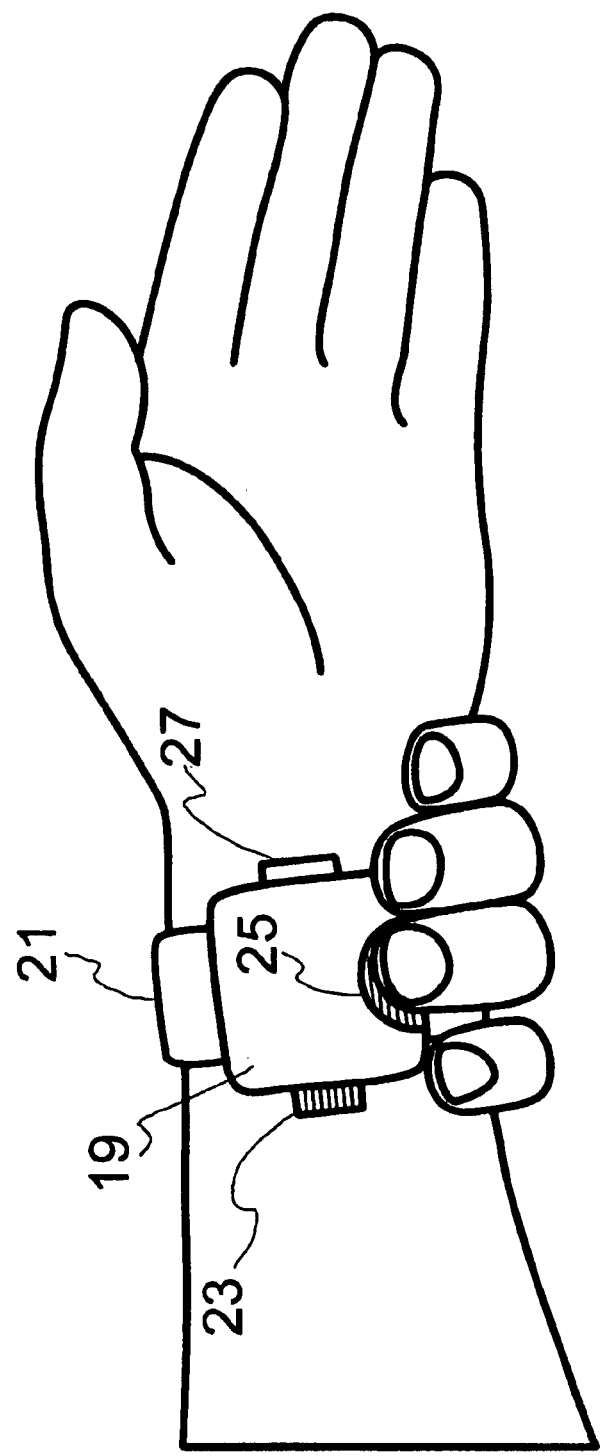
FIG. 3*b* is a pictorial diagram of the dispenser of FIG. 3*a* showing a convenient method of actuation.
Figure 4:
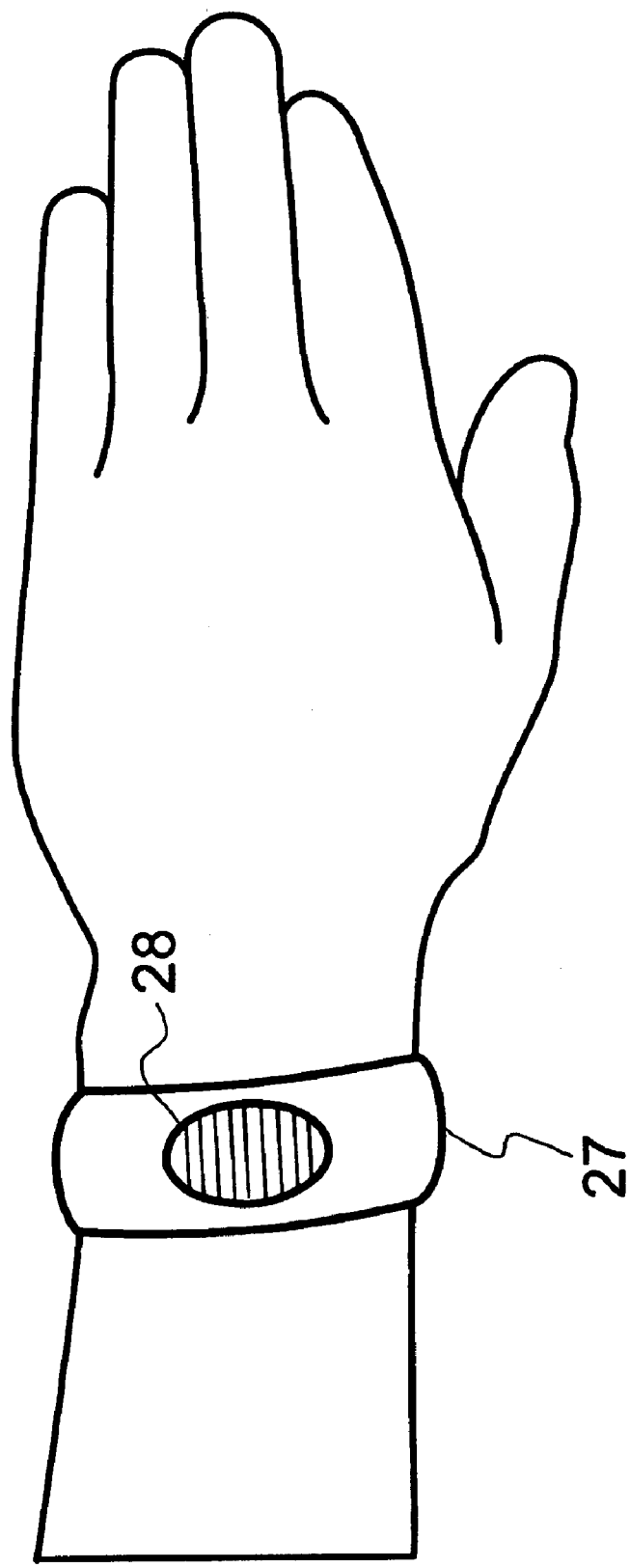
FIG. 4 is pictorial diagram of a hand treatment fluid-filled wristband usable with a dispenser such as that of FIG. 2.

A refinement of the device of FIG. 2 is depicted in FIGS. 3a and 3b showing a thin bladder 19 mounted on the underside of the wrist by wristband 21. The device is shown to have a nozzle assembly 27 and, optionally, a capped refill aperture 23. A finger depression area 25 is highlighted. Alternatively, the wristband itself can be part of the dispenser as shown in FIG. 4. A working fluid whether air or liquid can fill a portion or all of the wristband 27. Upon depression of the area 28 atop the wristband, pressure can be conveyed to the dispensing bladder underneath the wrist to cause a stream to be ejected into the hand. This can be especially effective by means of the pressure-multiplying dispenser discussed below. A three-dimensional depiction of the dispensing bladder is provided in FIG. 5a. The bladder 31 can be formed from soft, pliable plastic such as polyethylene or other plastic not attacked by the chemical constituents of the hand treatment. A nozzle assembly 32 is shown with a centrally-located nozzle aperture 33. The bladder 31 can be made integral with wristband 30 or as shown in FIGS. 5b and 5c, made attachable to the wristband. In FIG. 5b, the bladder 31 is shown attachable to the wristband 30 by Velcro component strips 34 and 35. FIG. 5c depicts the use of snap elements 36 on the wristband 30 that mate with the snap element counterparts on the side of the bladder. Another approach is to use clips that would attach to a wristwatch band.

Figure 6A:
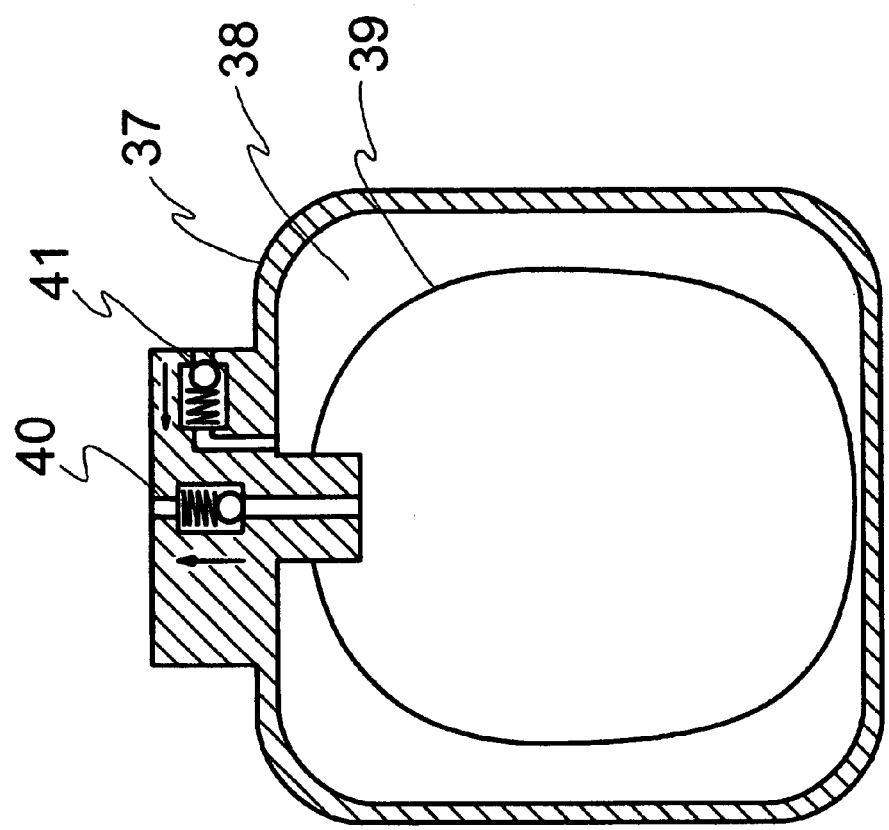
FIG. 6*a* is a cross-sectional view of a basic squeeze dispenser.

FIG. 6a is a cross-sectional view of a simple embodiment comprising a squeeze bottle 37. Internal to the squeeze bottle 37 are shown an air volume 38 and a hand treatment material-filled pliable bladder 39. Upon squeezing bottle 37, the pressure of air volume 38 is conveyed to material-filled bladder 39 so that the material is ejected from check valve-controlled channel 40. The check valve in this channel prevents leakage, but allows ejection of hand treatment material under pressure. Upon release of pressure to bottle 37, air is allowed to enter check valve-controlled channel 41 so as to replace the volume of hand treatment material ejected. The segregation of air and hand treatment material volumes permits the use of the device at any orientation with respect to gravity.

Pressure-multiplying Squeeze Dispenser

A more sophisticated embodiment of the invention makes use of a pressure-multiplying squeeze dispenser. Such a dispenser provides relatively high pressure ejection of fluid upon application of relatively little manual pressure. This allows good fluid stream formation and control over the stream trajectory to the target hand. For this reason, U.S. Pat. Nos. 4,4603,794 and 5,289,948 are hereby incorporated by reference thereto. In the first of these patents, the fundamental concept of a pressure-multiplying piston is disclosed. A pressure amplification is achieved that is equal to the ratio of the cross-sectional area of the pressure-multiplying piston to the cross-sectional area of a tube penetrating the pressure-multiplying piston.

Figure 6B:
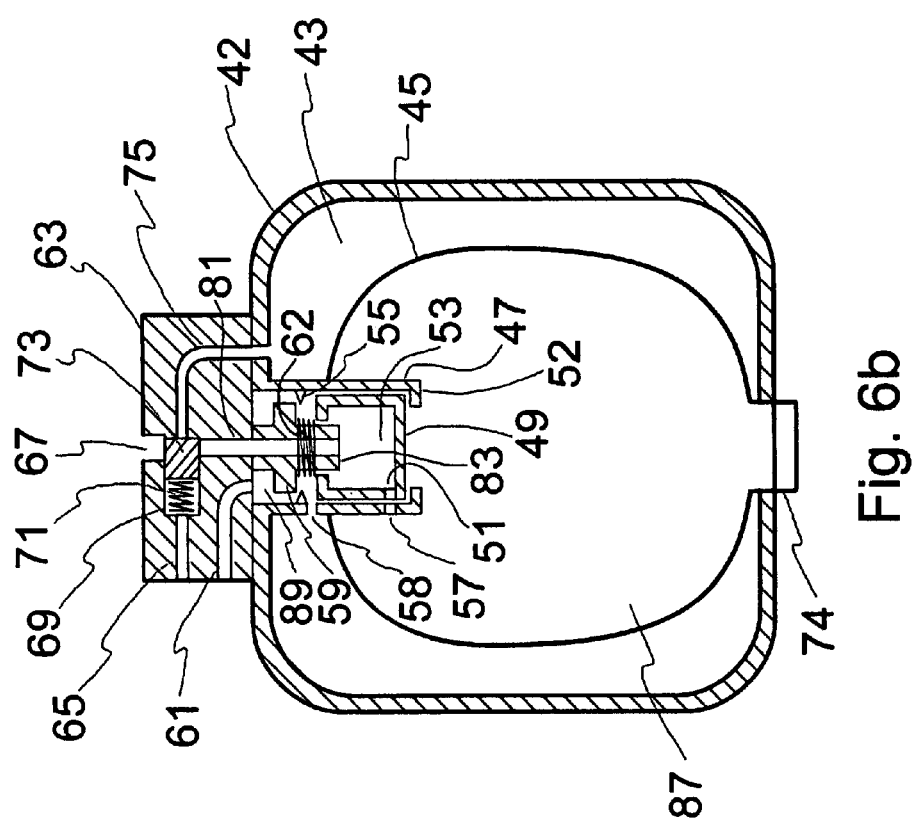
FIG. 6*b* is a cross-sectional view of a pressure-multiplying squeeze dispenser.

Necessary to the present invention is means to allow the dispenser to operate independent of its orientation with respect to the gravity field and the need to insure leak-proof operation. The pressure multiplying concept is adapted to the present invention to achieve these goals as shall be described with reference to FIG. 6b, a cross-sectional view of a pressure-multiplying version of the present invention. Shown is an outer bladder 42 having and output nozzle assembly 63 and a refill port with cap 74. Interior to the bladder 42 is an even more pliable bladder 45 that segregates the volume of the bladder 42 into an air-filled space 43 and a fluid-filled space 87. As can be appreciated, this is for the purpose of allowing operation independent of orientation with respect to gravity, in the same fashion as the embodiment of FIG. 6a. Upon compression of bladder 42, air in volume 43 causes compressive pressure on fluid-filled bladder 45. This pressure is transferred to fluid-filled movable cylinder 49 which translates within an outer guide cylinder 47. Cylinder 49 has been filled with fluid by virtue of port 51 on the side of cylinder 47 near its base. As cylinder 49 is caused to translate upward, port 51 is sealed by the wall of cylinder 47 so that the pressure of fluid 53 inside cylinder 49 is applied the end of tube assembly 83. Similarly, as cylinder 49 begins upward translation, air intake port 58 is sealed by the wall of cylinder 49 so that air in volume 89 is exhausted through channel 61. The pressure of the fluid in channel 81 of tube assembly 83 is increased over the pressure of the fluid in bladder 45 by the ratio of the cross-sectional area of cylinder 49 to the cross-sectional area of the end of tube assembly 83.

As cylinder 49 travels upward against the preload provided by spring 57 which is in turn captivated by spring seat 59, the air in volume 43 opens spring-loaded gate valve assembly 73 so as to allow fluid to be ejected from channel 81. Retaining protrusions 55 on the inside wall of cylinder 47 limit the upward travel of fluid-filled cylinder 49 in dispensing of a single dose of hand treatment. After the maximum amount of fluid in volume 53 of cylinder 49 is ejected at the limit of travel for cylinder 49 and upon removal of actuation pressure to bladder 42, cylinder 49 under spring tension travel back downward into bladder 45. Retaining flange 52 limits the downward travel of cylinder 47. As cylinder 49 descends, its interior is under a partial vacuum and upon exposure of port 51 to the fluid in volume 87 by way of port 57 in the wall of cylinder 47, the interior of cylinder 49 is refilled with liquid. At this same time, air intake port 58 in the wall of cylinder 47 is opened to allow air to enter volume 43 by way of volume 89 and channel 61.

Figure 6D:
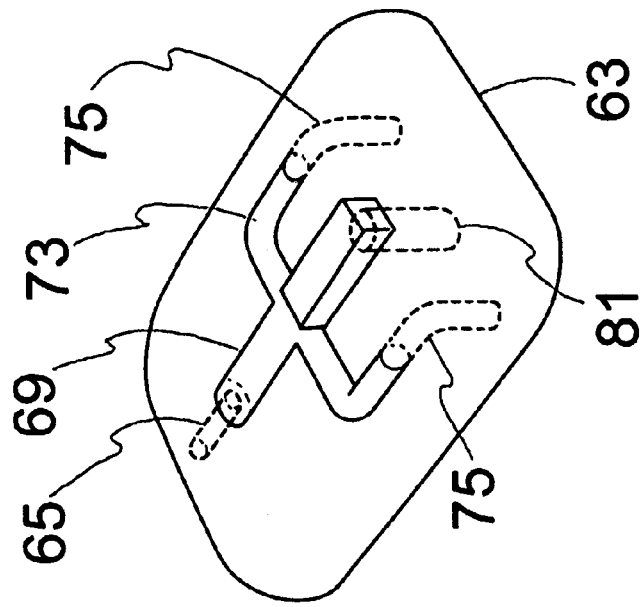
FIG. 6*d* is a pictorial view of the hidden components of the nozzle assembly of the pressure-multiplying squeeze dispenser.
Figure 6C:
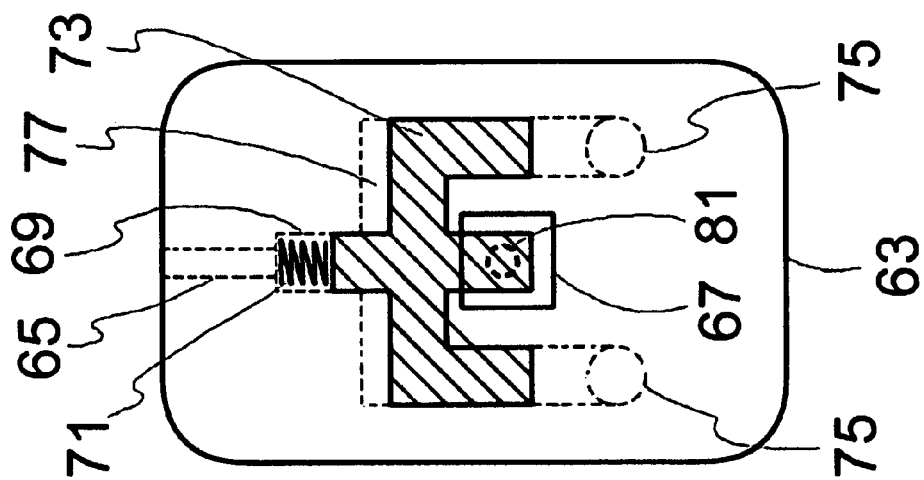
FIG. 6*c* is a plan view of components of the nozzle assembly of the pressure-multiplying squeeze dispenser.

FIGS. 6c and 6d serve to illustrate the function of gate valve assembly 73. In FIG. 6c, it can be observed that the gate valve assembly 73 is actually a mechanism with three forward prongs and one backward-directed extension held in a position which blocks fluid channel 81 by means of preload spring 71. The central forward prong has a rectangular or square cross section in contrast to the circular cross sections of the other prongs and the backward-directed extension so as to seat over the top of channel 81. Air pressure to displace the gate valve assembly 73 and open fluid channel 81 is applied only to the two outboard prongs of assembly 73 by way of air channels 75. Upon displacement of gate valve assembly 73, it occupies additional volume 77. Air channel 65 provides for release of air from spring compartment 69 upon progress of the backward-directed extension of assembly 73 into compartment 69.

Plunger-Type Dispenser

An alternative to squeeze dispensing makes use of a plunger. The way in which a plunger would be exploited in the present invention is shown in FIG. 7, a pictorial side view of such a device. In this embodiment, a fluid storage compartment 91 of the same form factor as the previously described squeeze bladder is likewise mounted on the underside of the wrist. A fluid dispensing plunger 93 is actuated by downward flexion of the hand at the wrist so as to depress plunger 93 with the base of the palm. With this motion, hand treatment fluid is ejected onto the base of the palm and both hands can be rubbed together to disperse the treatment.

Figure 8:
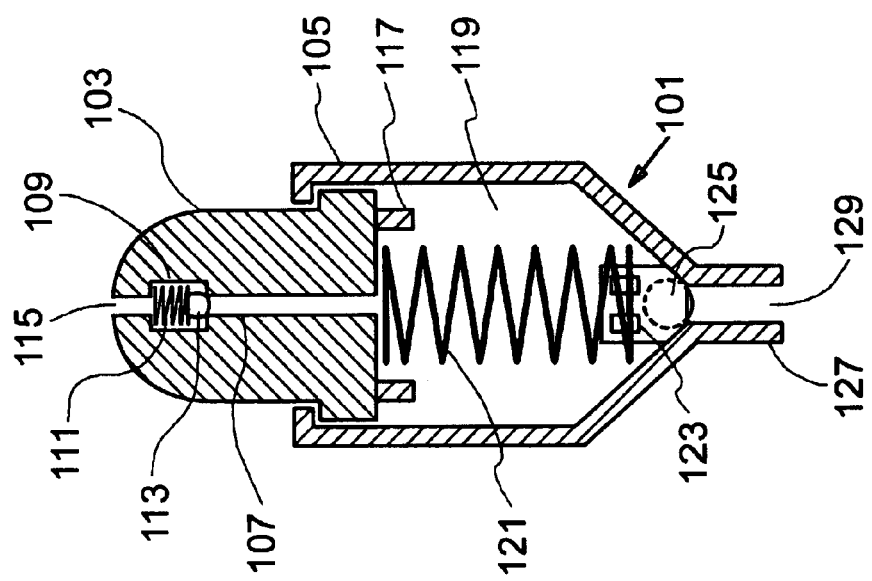
FIG. 8 is a cross-sectional view of a prior art plunger.

The type of plunger device 101 used on dish soap dispensers is shown in FIG. 8. A movable plunger 103 is spring loaded and captivated by housing 105. The preload spring 121 is seated against plunger 103 within cylinder 117. Tube 127 extends into fluid volume not shown. When the plunger 103 is depressed, air in volume 119 is impeded in downward flow by gravity check valve 125 having a cage 123 and is promoted in upward flow through channel 107 past spring loaded check valve 113. Upon release of plunger 103, a partial vacuum is formed in volume 119 which pulls fluid up through aperture 129 of tube 127 into volume 119 and onward up through channel 107 and out aperture 115. The tension of spring 109 is small, but sufficient to prevent unintended leakage of fluid. A miniature version of this plunger assembly can be fabricated for use as part of a plunger embodiment of the present invention.

Pressure-Multiplying Plunger-Type Dispenser

Figure 9A:
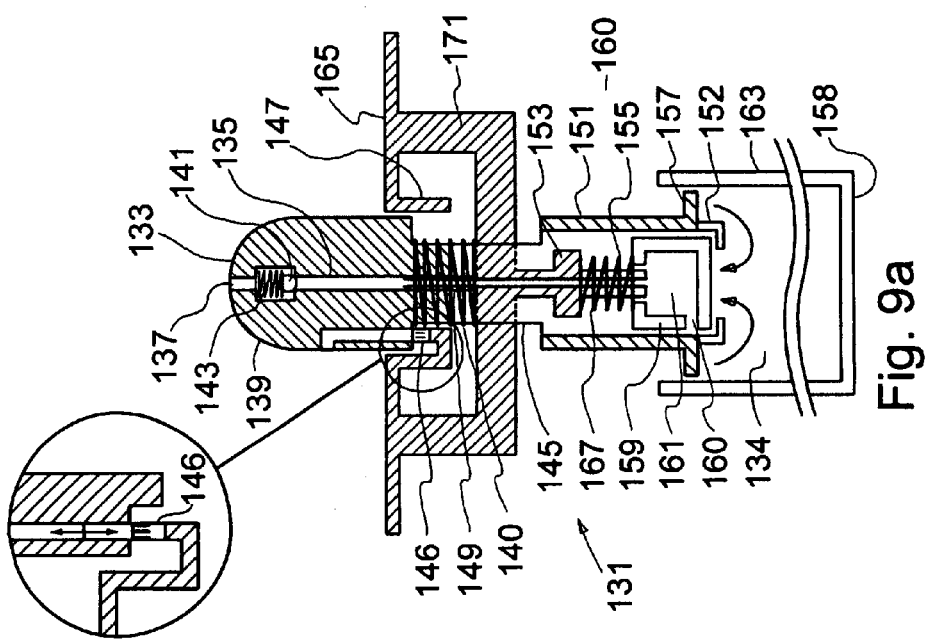
FIG. 9*a* is a cross-sectional view of a pressure-multiplying plunger dispenser.

Analogous to the pressure-multiplying squeeze dispenser is a pressure-multiplying version of the plunger device. A cross-sectional view of this device is shown in FIG. 9a. A movable plunger 133 has a preload tension from spring 140 that maintains its normal extended position. Spring 140 is seated against structural fins 171 internal to the dispenser. The plunger 133 has a central channel 135 that accepts the introduction of tube 149 connected by fins 171 to the dispenser housing 165, as plunger 133 is depressed. Cutouts 145 on the sides of plunger 133 admit the insertion of structural fins 171 which hold tube 149 in place. The lower portion of plunger 133 forms a cylinder 151 which houses a pressure-multiplying cylinder 159. Upon depression of plunger 133, the lower flange 157 of the plunger applies pressure to fluid volume 134 which in turn applies pressure to cylinder 159. This results in the upward travel of pressure-multiplying cylinder 159 and the high pressure ejection of fluid along channel 167 and channel 135, past check valve 141 and out through aperture 137. As the plunger 133 is depressed, the perforations of air intake tube 146 are sealed. Upon release of actuation pressure, plunger 133 returns upward by virtue of spring 140 and cylinder 159 returns downward under the influence of spring 155. Cylinder 159 refills with fluid as aperture 160 is in fluid communication with fluid volume 134. Near the limit of return travel for plunger 133, the perforations of air intake tube 146 are opened for air to refill volume 168. A flexible membrane 158 at the base of fluid container 163 allows air pressure in volume 168 to equilibrate with fluid pressure in volume 134. Retaining flange 152 limits the downward travel of cylinder 159. In FIG. 9b, the three-dimensional shape of plunger 133 is more clearly manifested. Shown are the cutout areas 145 which are penetrated by the structural fins 171 which hold tube 149 in fixed disposition with respect to the dispenser housing 165.

Nozzle Configurations

In the simplest embodiment, the nozzle of the present invention is of a fixed geometry. Other embodiments include retractable or extendible versions, as well as nozzles that can be adjusted in direction and those which allow selection of the output flow type from streaming to spraying. Adjustable nozzles can be implemented for pressure-multiplying dispensers with some increase in complexity over counterparts for non pressure-multiplying dispensers.

In various embodiments of the present invention, the nozzle will be oriented to provide unobstructed dispensing of hand treatment to the target hand. For the case in which hand treatment is to be dispensed to the hand of the arm upon which the dispenser is mounted, this can be accomplished even when the user is wearing a long-sleeved shirt or blouse, or a jacket. In situations where a garment might obstruct dispensing, it could be efficacious to have an extendible nozzle. An example of such a nozzle is shown in FIG. 10. A cylindrical nozzle body 201 is shown with ring embossments 203. A complementary ring depression 205 is present in the neck 207 of the dispenser so that longitudinal motion of the nozzle body 201 relative to the dispenser neck 207 establishes a fixed number of detint positions.

As dictated by the preference of the user of the invention, the type of flow of dispensed material can be selected in an embodiment with flow control means. Numerous prior art examples of variable flow nozzles are extant in the patent literature; examples include U.S. Pat. Nos. 3,843,030, 3,967, 765, and 4,234,128. These nozzle designs exhibit variable flow geometry. An attending alteration in the flow from a streaming to spraying nature occurs upon rotation of one of the component members of the nozzle relative to the other. In FIG. 11, this type of nozzle is shown in the context of the present invention. A fixed nozzle component 223 is attached to the dispenser body 221. Rotation of the movable nozzle component 225 results in variation in the type of flow. In such an implementation, the flow channel is segmented into two portions and the alignment of a particular cross-sectional geometry of each of these portions of the channel is used to adjust the nature of the flow. Another method of varying the type of flow is that used in typical garden hose nozzles in which a flow output aperture is variably occluded by the longitudinal translation of a conical member with its apex directed into the flow output aperture by a screw motion.

Cartridge- and Pump- and Plunger-Based Embodiments of the Invention

Figure 13:
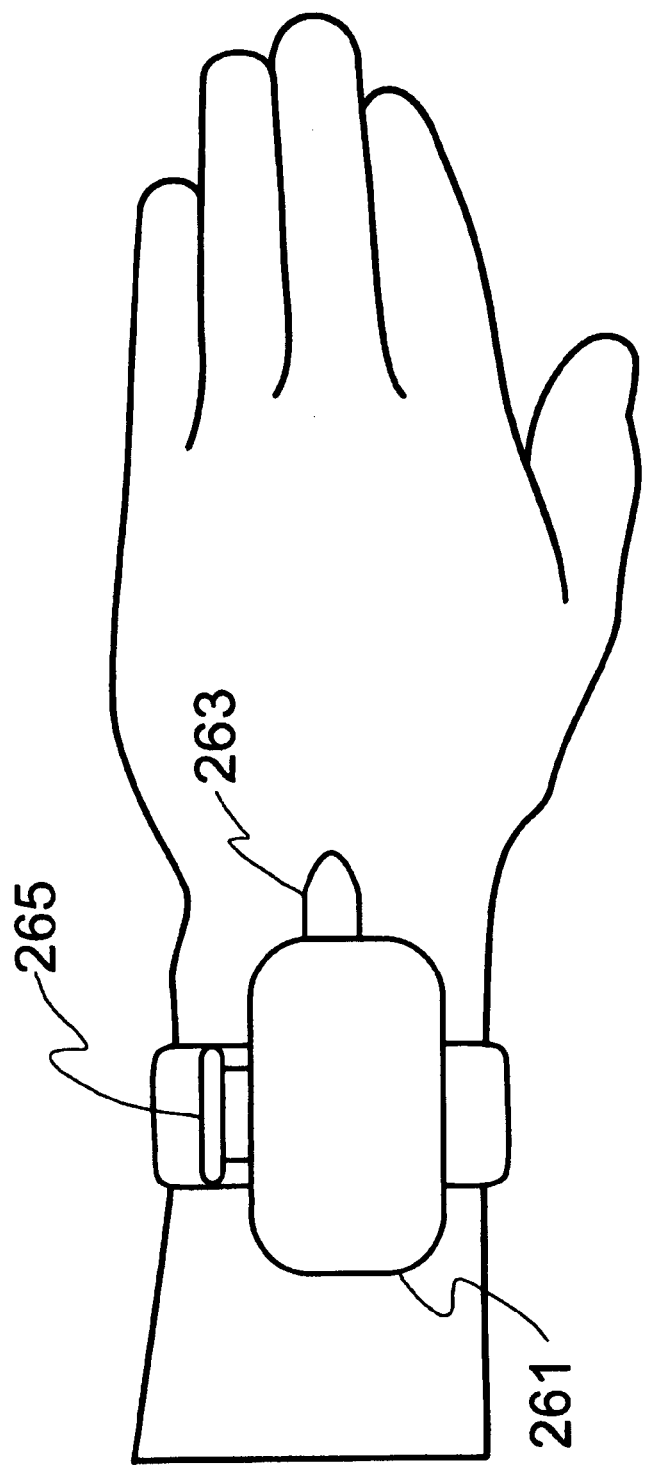
FIG. 13 is a pictorial view of a plunger-based dispenser having the plunger oriented perpendicular to the fluid ejection axis.
Figure 14:
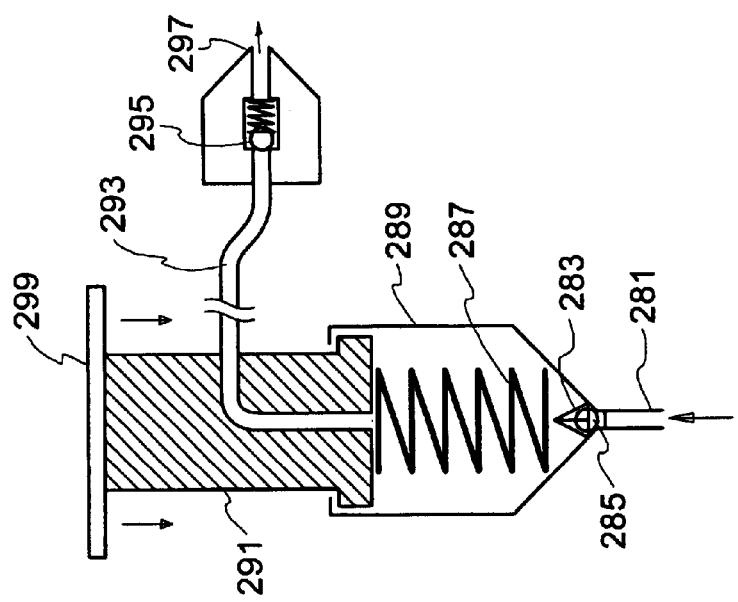
FIG. 14 is a cross-sectional view of the plunger and nozzle assembly of the dispenser of FIG. 13.

A dispenser detachable from a wristband is shown in FIGS. 12a through 12c. Depicted are wrist mounted, detachable dispensers. FIG. 12a shows a pump spray type dispenser 241 mounted on top of the wrist. Flange 243 allows the depression of the end of the dispenser column to eject material from the nozzle 245. FIG. 12c depicts a detachable capped bottle. The cap 247 can be one which pops off, but is retained in connection with the dispenser by a plastic link. FIG. 13 depicts a pump spray bottle 261 in which the pump actuator flange 265 is mounted at 90 degrees to the axis of the spray nozzle 261. This can improve the ease of actuation by the fingers of the alternate hand. FIG. 14 depicts a naive means of implementing the dispenser of FIG. 13. When depressed, the actuation flange 299 with attached plunger 291 compresses spring 287 and reduces the free volume of plunger-containing body 289. Upon release of depressed actuation flange 299, the plunger 291 retracts creating a suction on inlet port 281 to intake fluid which fills plunger-containing body 289 and proceeds to travel through flexible tube 293 for ejection from nozzle 297. Check valves 283 and 295 prohibit deleterious flow of fluid.

Figure 15:
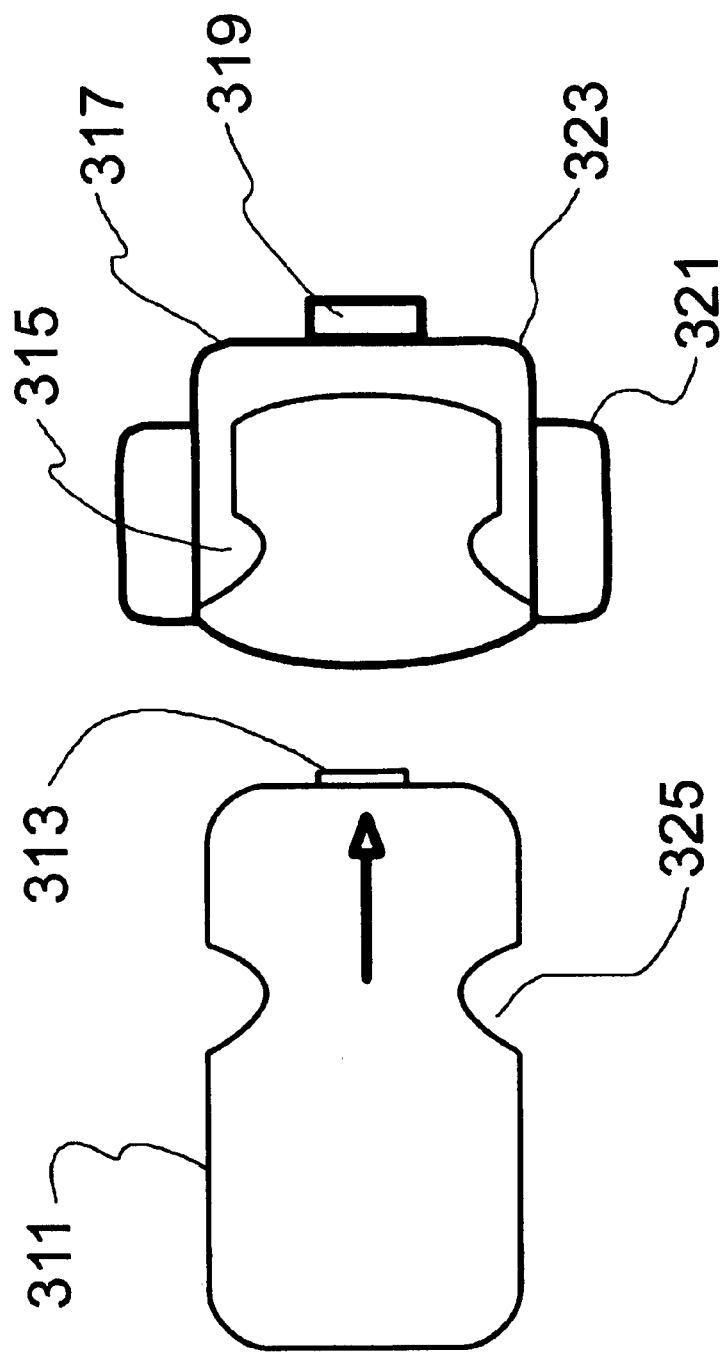
FIG. 15 is a pictorial view of a cartridge-based dispenser.

FIG. 15 depicts a cartridge-based dispenser showing the disposable hand treatment-containing cartridge 311 having indentations 325 and easily punctured, self sealing dispensing port 313. The wrist-mounted holder 323 is shown having flexible side fingers 315 which seat in indentations 325 for retaining an installed cartridge 311. The body of the holder 317 has a base plate to which is attached wrist band 321. As is well known in the prior art, the cartridge 311 can be inserted into the holder 317 so as to provide leak-free dispensing of fluid through nozzle 319 upon squeezing of a deformable portion of cartridge 311.

For children, the dispenser can be in the shape of or be embossed with the logos of sports teams, super heroes, or cartoon icons. Further, dose-delivering dispensers in the shape of cartoon characters or refillable cartridge-based dispensers are feasible. With a cartridge or refillable dispenser other functions can be added to the dispenser such as having LEDs on them that light up with use. High brightness, low current LEDs as used on cell phones are quite striking. Consideration of a time delay for sequential dispensing so that children would be less inclined to waste the hand treatment material. By this, is meant that it would take a minute or two before you could dispense a second dose.

This could be achieved by establishing the time constant for repressurization of the bladder using a suitably small sized air hole.

Figure 16:
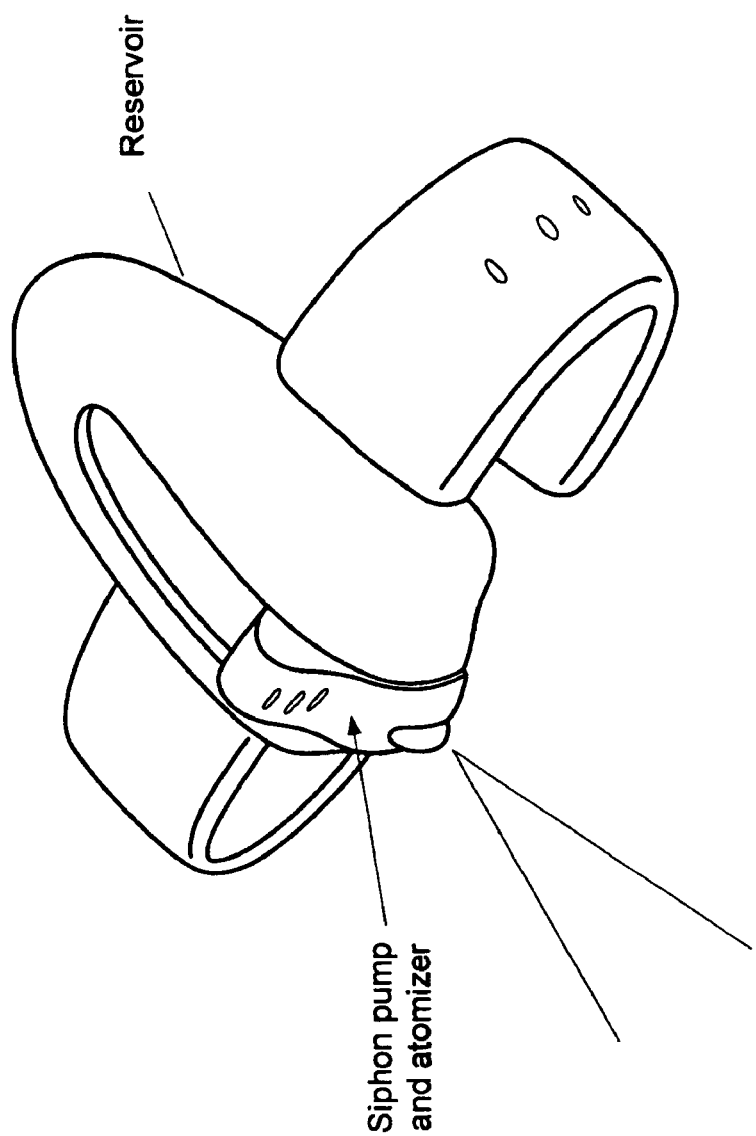
FIG. 16 is a pictorial view of a siphon pump-based dispenser ejecting fluid perpendicular to the longitudinal axis of the arm.
Figure 17:
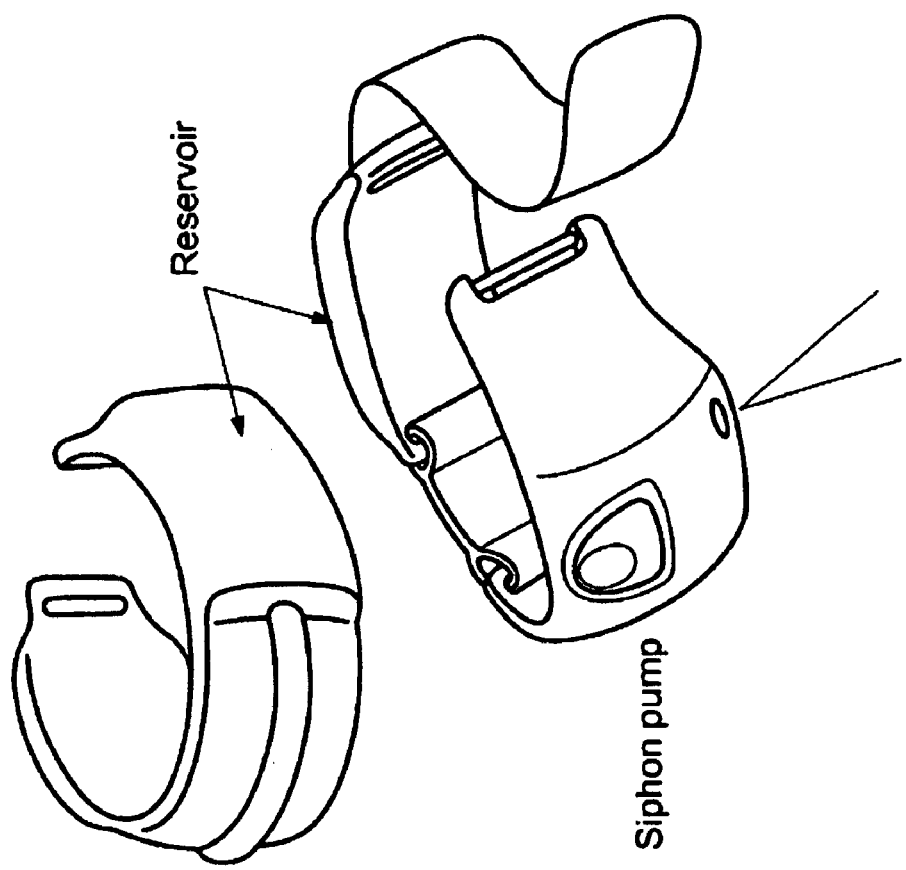
FIG. 17 is a pictorial view of a siphon pump-based dispenser ejecting fluid parallel to the longitudinal axis of the arm.
Figure 18:
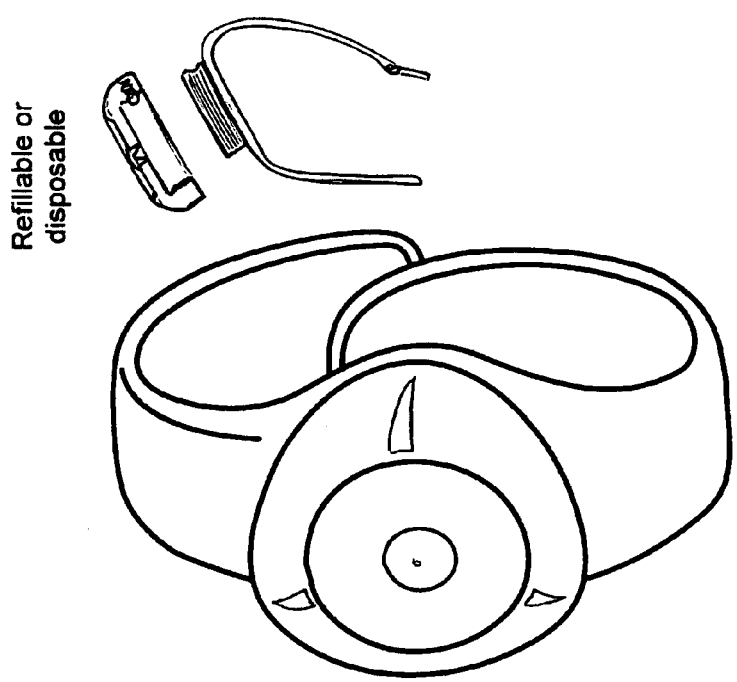
FIG. 18 is a pictorial view of a screw mechanism-based dispenser.
Figure 19:
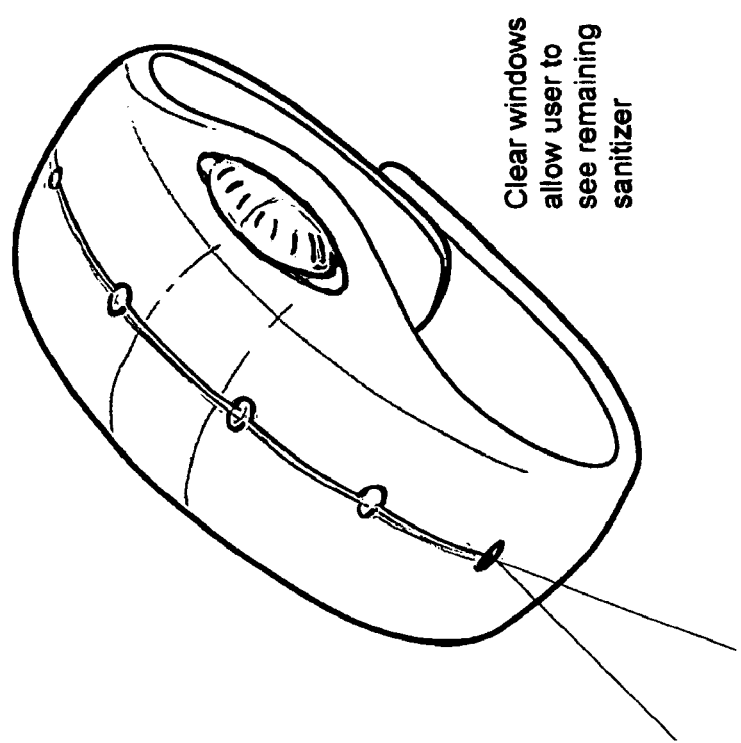
FIG. 19 is a pictorial view of a thumbwheel-actuated dispenser.
Figure 20:
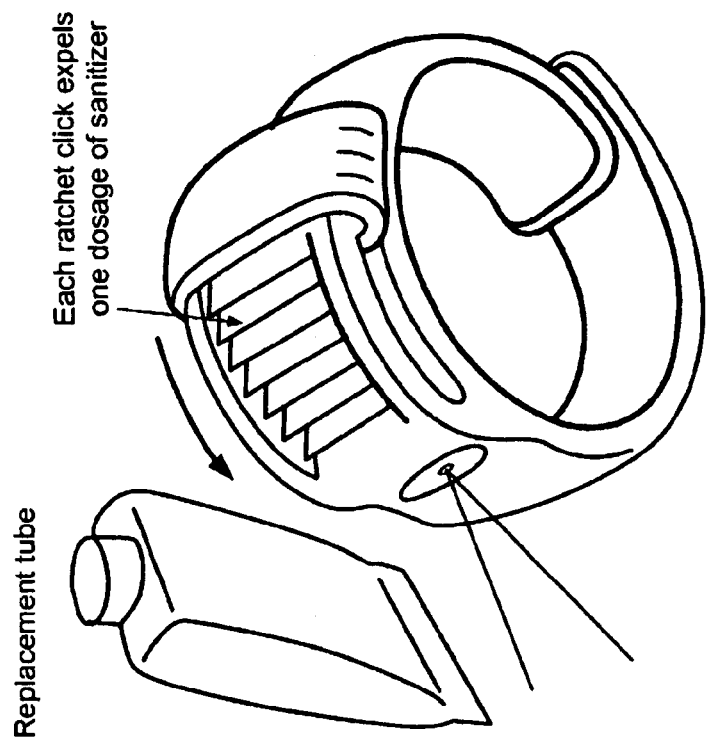
FIG. 20 is a pictorial view of a ratchet mechanism-actuated dispenser.
Figure 21:
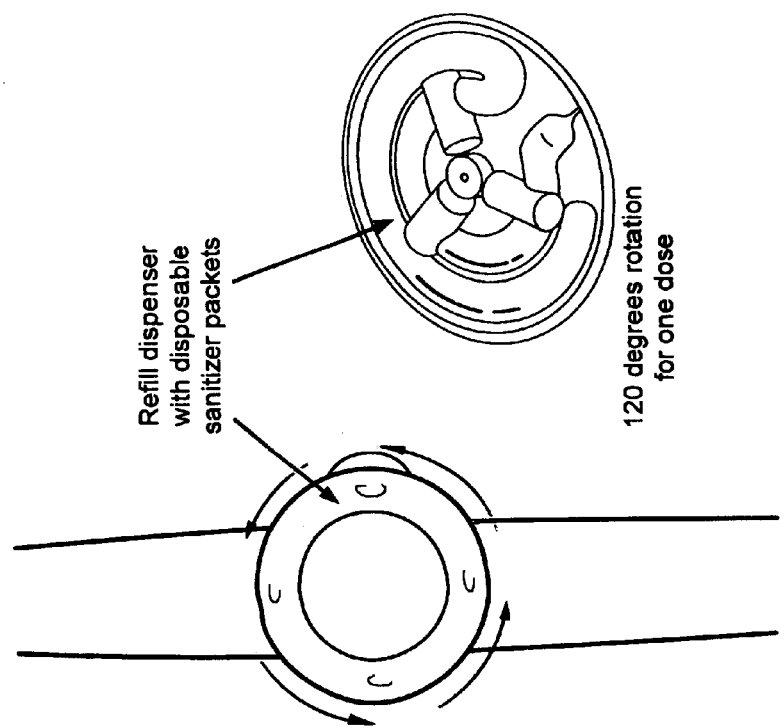
FIG. 21 is a pictorial view of a rotary compression-based dispenser.
Figure 22:
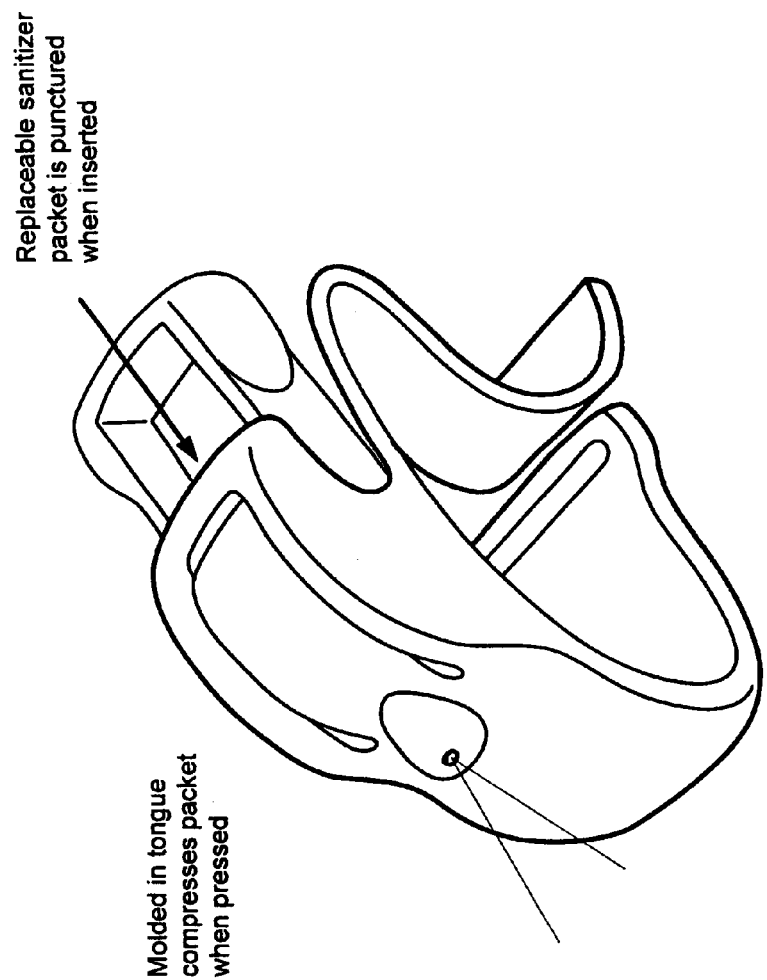
FIG. 22 is a pictorial view of a direct compression-based, packet-refillable dispenser.

A number of more refined embodiments of the wrist mounted dispenser of hand treatments are shown in FIGS. 16 through 26. FIG. 16 depicts a siphon pump design that would be actuated by thumb pressure against a sliding actuator. Spray is ejected from the end of the actuator as fluid is siphoned from the reservoir. Another form factor for the siphon pump is provided in the design of FIG. 17 wherein the actuator is in the form of a button that can be depressed to cause ejection of hand treatment. In the designs of both FIGS. 16 and 17, two one-way check valves are employed as is common practice in the art. The design of FIG. 18 exploits a screw thread mechanism to exert pressure on a fluid. As the outer housing comprising both piston and one-way valve is rotated to cause fluid compression, the fluid is exhausted through the valve. A screw drive mechanism similar in function to those found in stick deodorant dispensers is depicted in the design of FIG. 19. A ratchet clip mechanism is used in the design of FIG. 20 to squeeze hand treatment fluid from a tube that is captivated by ratchet housing. In FIG. 21, a design is shown which exploits a roller pump mechanism. Each incremental turn of the dispenser dial would cause a fraction of the contained fluid to be ejected while prevented leakage past the seal maintained by the rollers. A simple, direct pressure mechanism is used in the design of FIG. 22 to squeeze hand treatment fluid through a one-way valve, similar to an instant glue dispenser.

Additional Embodiments

Figure 23:
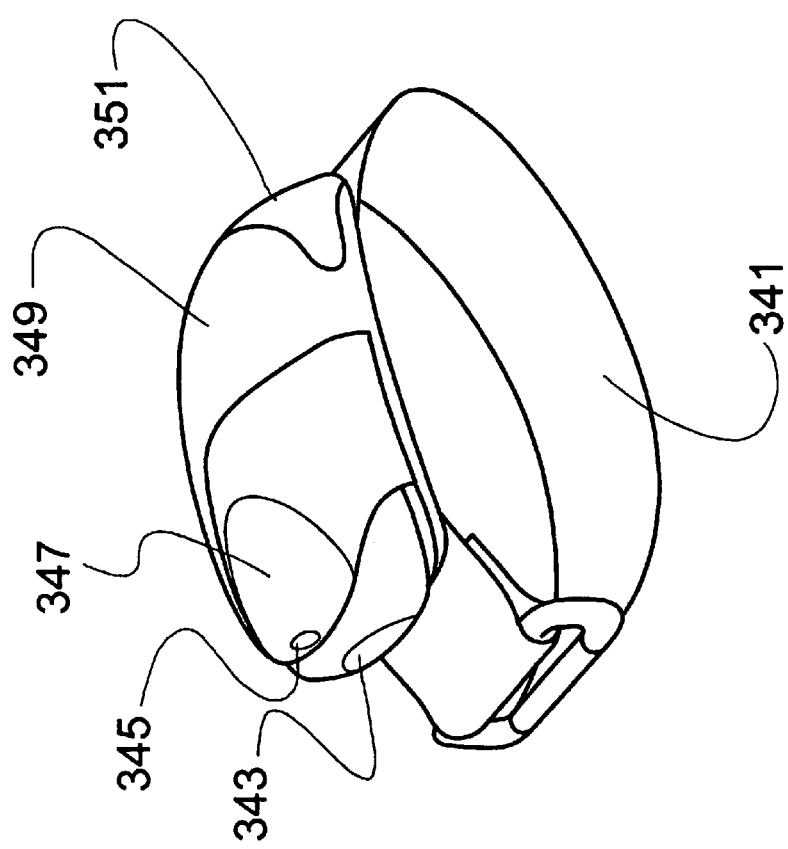
FIG. 23 is a pictorial view of refillable, of a first push button-actuated dispenser.

FIG. 23 is a pictorial diagram of dispenser using the basic principle of FIG. 16. Hence, the depicted device dispenses hand treatment fluid to the hand of the arm which does not have the dispenser attached. The ejection axis for dispensing is perpendicular to the longitudinal axis of the arm to which the device is attached and fluid is dispensed onto the fingers of the actuating hand. The cross sectional view of the device is provided in FIG. 24. With respect to FIG. 23, the dispenser body 349 is shown attached to wristband 341. It comprises a hinged lid 351 that contains a hand treatment fluid refillable volume. Depression of spring-loaded pump button 343 causes the ejection of hand treatment fluid through nozzle 345.

Figure 25:
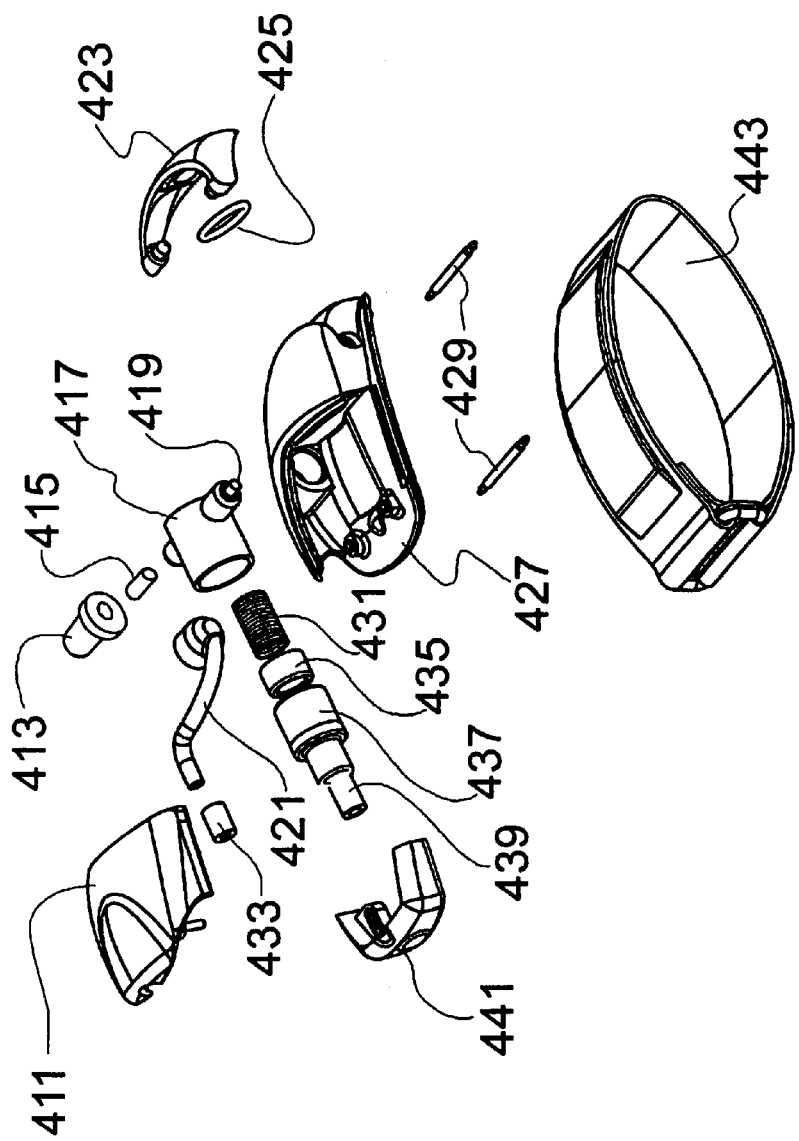
FIG. 25 is an exploded diagram of the components of the dispenser of FIG. 23.

FIG. 25 is an exploded diagram of the components of this embodiment. The upper housing 411 provides a means of enclosing, retaining, and protecting the pump assembly and actuation components. It secures actuation button 441 to lower housing 427 via interlocking pin and slot feature and retains the dispensing nozzle 433. The actuation button 441 is the primary user interface for activation of the device. The contour shape is designed to accommodate a discreet, "no-look" actuation. The piston shaft 439 is the main mechanical link between the actuation button 441 and the pump piston 435. Piston housing 437 provides precise cylinder bore for high compression dispensing of hand treatment fluid. Mechanical means of pressurizing the pump chamber 417 via displacement of actuator button 441 is provided by piston 435. It displaces hand treatment fluid through the exit port of pump chamber 417 on the dispensing stroke and provides negative pressure to draw fresh hand treatment fluid from the reservoir contained in lower housing 427 on the intake stroke. The return force necessary to drive piston 435 through the intake stroke is provided by return spring 431. Main pump chamber 417 provides the main cylinder for pressurization during dispensing and intake strokes. It integrates the valve mating surface for the exit check valve 419 and retains piston housing 437 via precision friction slip fit. An inlet port 413 provides a precision sealing surface between the reservoir and inlet check valve 415 which seals the inlet port 413 during the dispensing stroke and hence stops hand treatment fluid backflow into the reservoir. Exit check valve 419 provides a means of sealing the pump chamber 417 during the inlet stroke, preventing air intake through dispensing nozzle 433 to reduce or eliminate pump cavitation. This nozzle establishes a calibrated orifice through which a metered dosage of hand treatment fluid can exit the dispenser. An exit tube 421 routes hand treatment fluid to the dispensing nozzle 433 and provides a means of retaining the exit check valve 419. The lower housing 427 retains the upper housing 411 and actuation button 441. It also houses the main fill port for refillable dispensers. Enclosing and sealing the main fluid reservoir is the reservoir fill lid 423. It is easily released for refilling by an ergonomic snap feature at its leading edge. O ring 425 provides additional sealing at the fill port by compressing when fill lid 423 is snapped shut. It also provides a barrier which reduces or prevents evaporation of fresh hand treatment fluid. Band pins 429 provide attachment of the dispenser assembly to the wristband 443.

Figure 24:
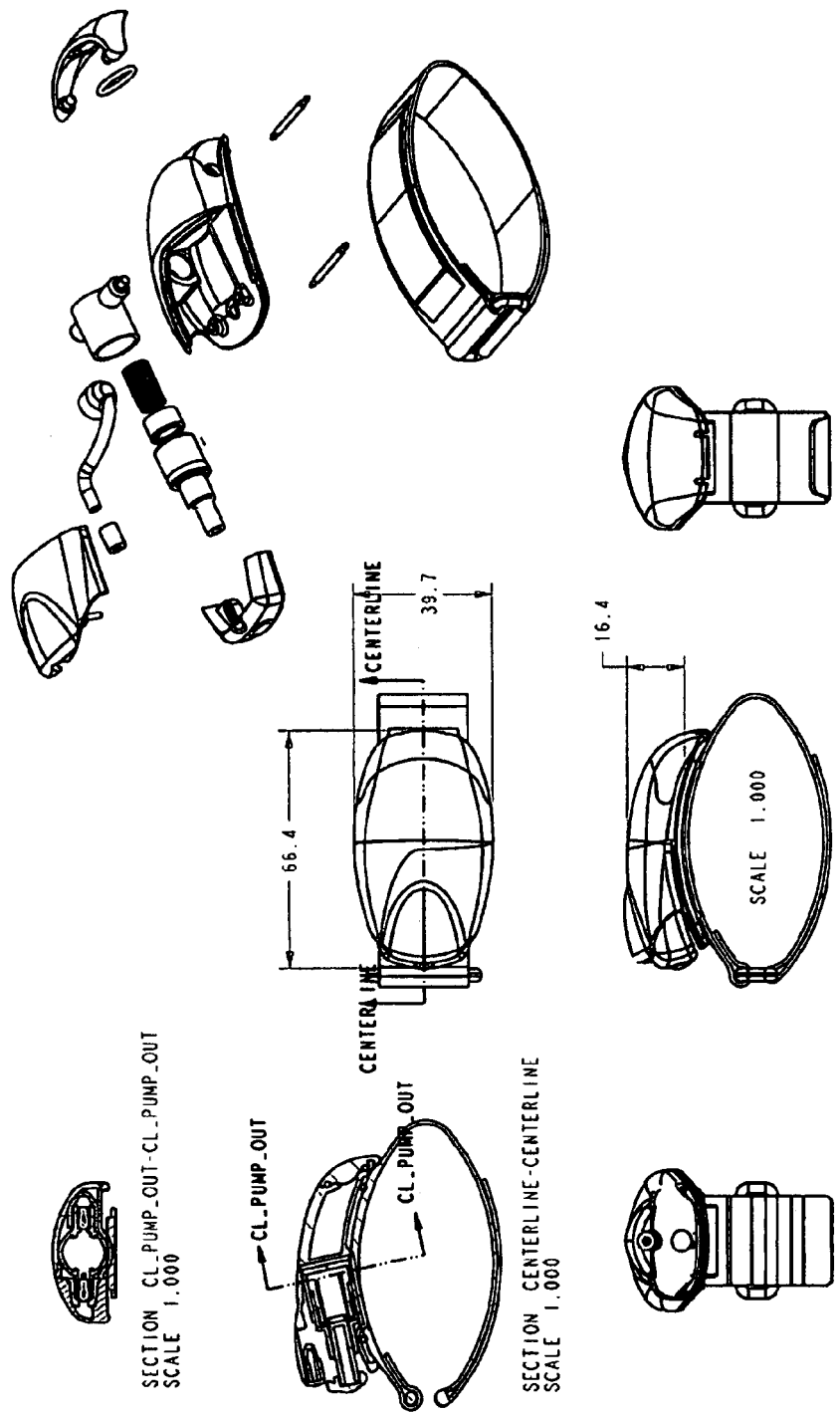
FIG. 24 is a cross-sectional view of the dispenser of FIG. 23.
Figure 26C:
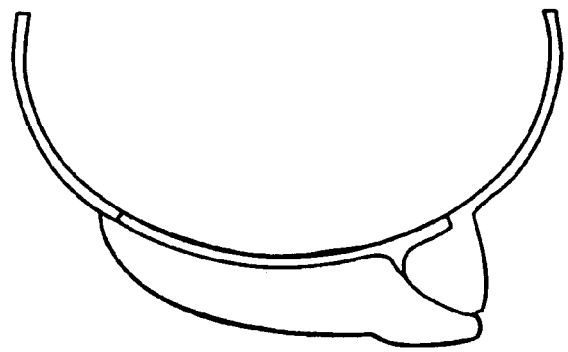
FIG. 26*a* is a pictorial view of refillable, of a second push button-actuated dispenser having a functioning watch face.
FIG. 26*b* is a cross-sectional view of the dispenser of FIG. 26*a*.
Figure 26B:
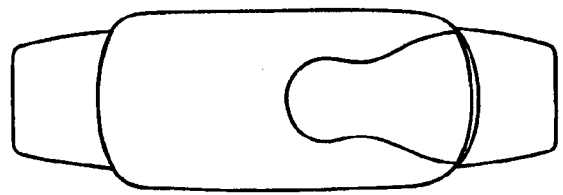
Figure 26A:
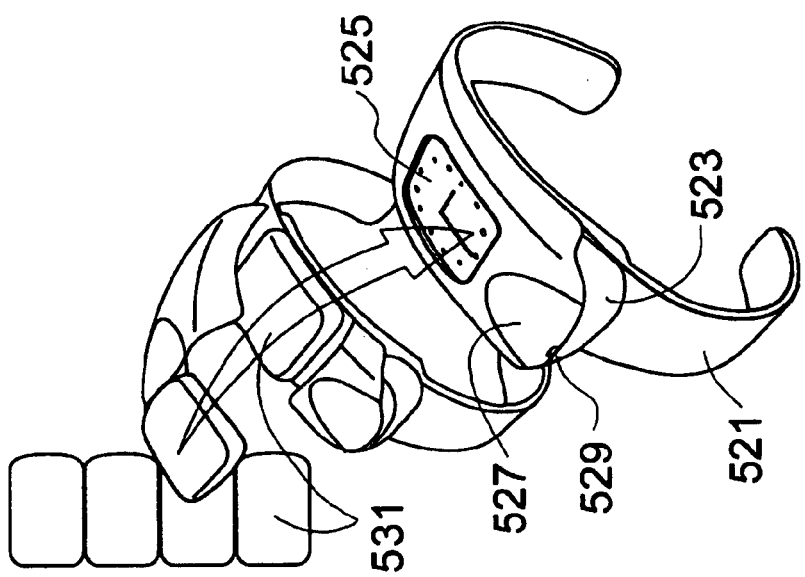

FIG. 26a is a pictorial diagram of dispenser similar to that of FIGS. 23 through 25. Shown is a functional watch face atop the dispenser top 527. Also, in lieu of a fluid reservoir, cartridge packets 531 are used in this embodiment. The cross sectional view of the device is provided in FIG. 26b. With respect to FIG. 26b, the dispenser body is shown to be part of a wrist ring 521. It comprises a hinged top 527 that contains removable sanitizer-containing packet 531. Upon insert of packet 531 and closure of hinged top 527, the packet 531 is punctured by channel inlet 533. Retraction of spring-loaded pump button 523 creates a partial vacuum in cylinder volume 535 which is filled through channel 537 by sanitizer fluid from packet 531. Upon depression of pump button 523, backflow through channel 537 is prevented by check valve or other means and the fluid in volume 535 is forced through channel 539 and ejected from nozzle 529.

It is to be understood that a plethora of cartridge or packet designs and form factors are within the scope of the present invention, including color-coded packets that can distinguish the type or strength of hand treatment contained therein. Also within the scope of this invention are various means to dispense hand treatment material from such packets including the mechanisms for extracting the hand treatment material from said packets. Extraction mechanisms can invoke pressure (internal or external to packet) or suction.

Another category of embodiments of the present invention comprise those dispensers that are either attachable to wristwatches or are part of wristwatches or wristwatch bands. FIG. 27 depicts wristwatch 571 and band 573. A hand treatment dispenser 561 is attachable to the wristband by means of a Velcro surface 563 that mates with a complementary Velcro surface on the underside of the wristband 573. The dispenser 561 is shown having a push button 579 actuator that dispenses a spray 577 of hand treatment.

Pluralities of alternate attachment schemes are possible for dispensers of varying form factor. Examples of other attachment schemes include magnetic means, mechanical clips, loops, slide inserts, etc. Various types of dispensers can be made attachable including disposable, and refillable as in the case of packet dispensers described above.

Figure 29:
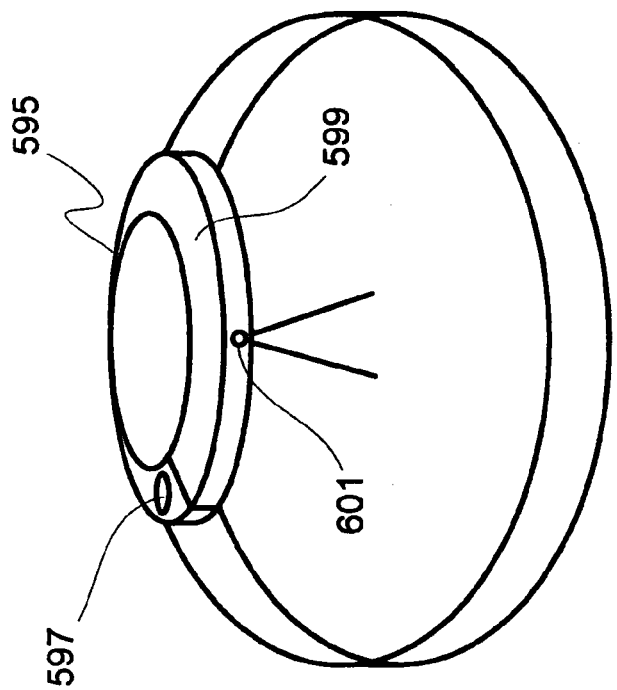
FIG. 29 is a pictorial diagram of a dispenser that is integral to the construction of a wristwatch.
Figure 28:
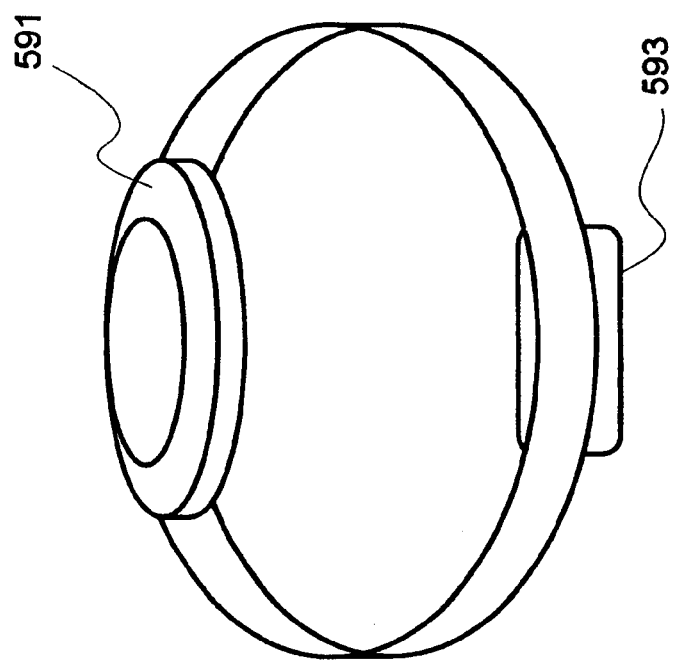
FIG. 28 is a pictorial diagram of a dispenser permanently attached to a wristwatch band.

FIG. 28 depicts a dispenser 593 that is manufactured as part of the wristband for watch 591 and hence would be refillable. Other schemes for fabrication of the dispenser integral to the wristband include fabricating a wristband that serves as the reservoir for hand treatment fluid and the placement of the dispenser actuator at differing positions along the wristband. FIG. 29 depicts a dispenser that is made part of the wristwatch body 595. A hinged lid 599 houses the refillable dispenser packet not shown. An actuation button 597 is depressed to cause a stream of hand treatment material to be ejected from nozzle 601.

Figure 30:
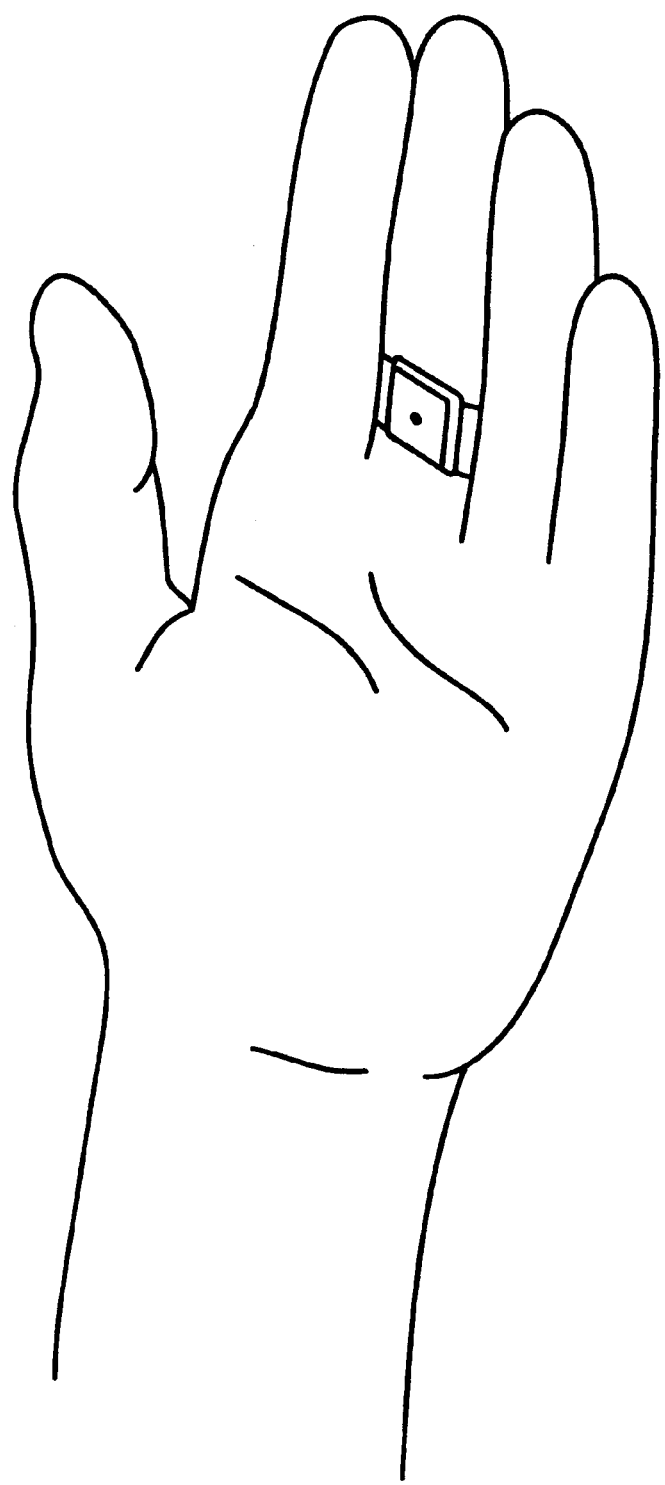
FIG. 30 is a pictorial diagram of a dispenser mounted to a finger of the hand.

FIG. 30 depicts a finger-mounted dispenser 631 mounted on a finger band or ring 633 and having a dispensing aperture 635. Any number of the aforementioned actuation schemes can be used in this device, so that simple compression of the exposed face of dispenser 631 will yield ejection of fluid from aperture 635.

Dispenser Types Using Other Mechanisms

Among other dispenser types are drip, pressurized, and pump-driven versions. Drip type dispensers are of limited practicality given that they are orientation sensitive. One way in which such a dispenser could be used involves actuating a shutoff valve. Various approaches well known in the prior art can be used to actuate the opening of such a valve by hand pressure. Subsequent to opening the valve, it is required to orient the dispenser to allow hand treatment to drip into the hand.

Borrowing from the technology used in the fabrication of pressurized shaving cream dispensers, there are well known methods of producing gas-pressurized streams of liquids and gels. The dispenser exploiting gas pressurization could be a low profile metal, disposable cartridge that removably attaches to a wristband.

Applicable miniature electromechanical schemes that could be used for ejecting hand treatment material are well known in the prior art. Foremost among electromechanical actuation methods is that of a solenoid. The miniature solenoids used in ink jet printing can be applied to discharging small jets of fluid. Sufficient electrical energy for hundreds of actuations can be contained in small form factor batteries such as those of the disc lithium variety. Alternatively, miniature diaphragm pumps and piezoelectric pumps used for insulin delivery can be used for discharge of small jets of fluid. Finally, in the category of thermoelectric devices, Peltier effect devices can be used with working fluids or phase change materials to effect large pressure changes with modest electrically-induced temperature changes and thereby eject fluids upon initiation of current flow into the Peltier device. In all electrical methods, a consistent fixed dosage of ejected hand treatment material can be established by electronically fixing the duration of the governing voltage or current pulse. Remote control actuation is imminently feasible with commercially-available low power consumption micro-transmitters and receivers. There are numerous ways in which such remote control can be executed, typically using the free hand or other part of the body.

A final concept is that of a dispenser similar to that of Listerine oral patches that dissolve in the mouth. Such a dispenser would dispense a sanitizing compound in the same form as the Listerine thin film, but which would disperse on the hands. Because the dispersal cannot rely on water, a particular formulation containing alcohol, perhaps using long chain hydrocarbons in concert with ethanol, would need to be used. Such an alcohol-based formulation could be a thin film formable solid until liquefied by the friction/pressure (rather than heat) of rubbing hands together.

While there have been shown and described the preferred embodiments of the present invention, it is to be understood that the invention can be embodied otherwise than is herein specifically illustrated and described and that, within such embodiments certain changes in the detail and configuration of this invention, and in the form and arrangements of the components of this invention, can be made without departing from the underlying idea or principles of this invention within the scope of the appended claims.

Preferred Embodiments Of the Wearable Dispenser

Neck-worn and disposable wrist worn embodiments offer great convenience, both for disposable and non-disposable versions. The neck-worn embodiments rely on spring-loaded pump mechanisms for dispensing of skin treatment material from a nozzle upon depression of an actuation button. In the case of a foam dispenser, the actuator assembly also dispenses the foam. For the disposable wrist-worn embodiments, low manufacturing cost diaphragm valves are used with a simple deformable container. Following are descriptions of variations of these two types of dispensers.

Neck-worn Embodiments

Figure 31:
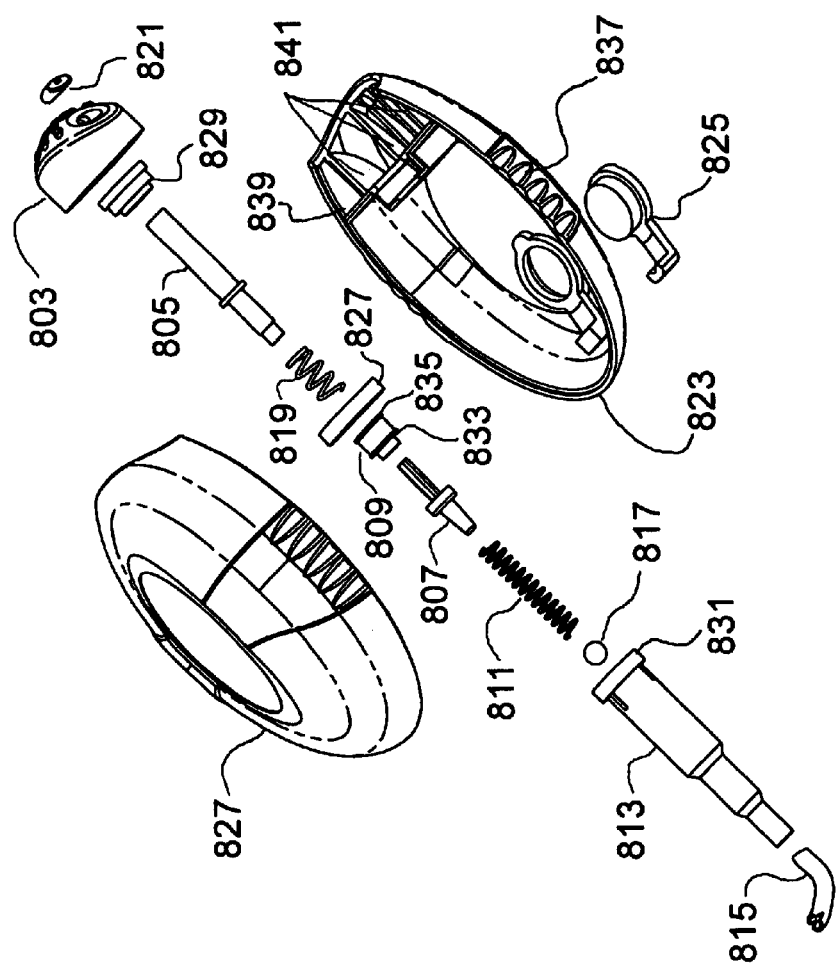
FIG. 31 is an exploded diagram of first version of a neck-worn dispenser.
Figure 32:
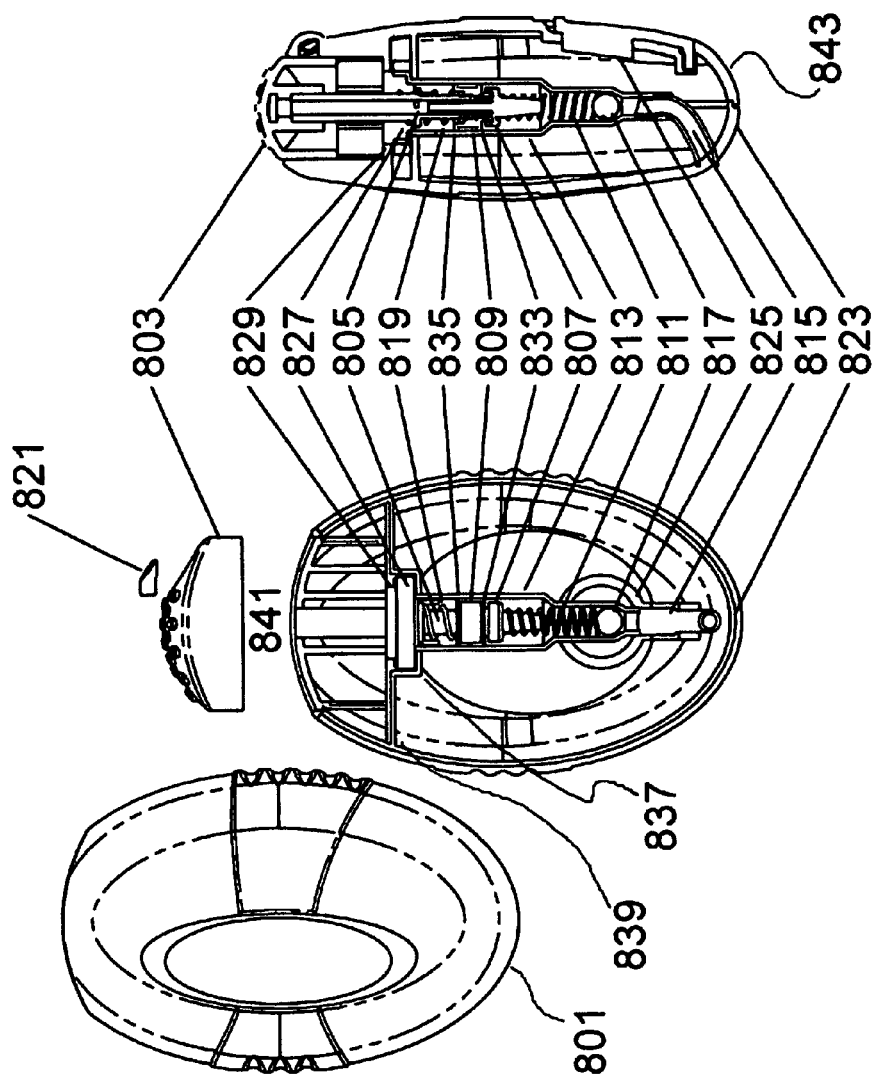
FIG. 32 is an assembled and cross-sectional view of the first version of a neck-worn dispenser.

FIGS. 31 through 37 depict versions of neck-worn dispensing devices. FIG. 31 is an exploded diagram of a first version that dispenses skin treatment material from an actuation button 803 located at one end of the device. Shown is an upper housing 801 that provides means via internal rib geometry, for enclosing, retaining and protecting the pump assembly and actuation components. It also secures actuation button 803 to lower housing 823 via interlocking part geometry and secures location of the pump via rib geometry which has mating interface to pump geometry. Other features of the upper housing 801 include provision for location of brand/model identification or logo, an external rib geometry for tactile grip and/or purchase, a zone to over-mold soft touch elastomer material for additional tactile feedback, half of reservoir capacity for fluid or treatment material to be dispensed. The upper housing 801 can be secured to lower housing 823 via friction fit, sonic weld, chemical bond or mechanical fastener. Actuation button 803 is the primary user interface for activation of the dispensing device. It provides hollow internal geometry to allow cleanser fluid to pass through and be directed to dispensing nozzle 821. The contour and shape of button (including tactile feedback feature) is designed to accommodate "no-look" actuation. A recess is provided in the button 803 to accommodate integrated dispensing nozzle 821. The actuation button 803 attaches to piston shaft via friction fit, sonic weld or chemical bond. Piston shaft 805 serves as the main mechanical link between actuation button and pump piston. Its hollow shaft allows fluid to move up to activation button 803 to be dispensed at nozzle 821 and provides flange geometry to create bearing flange for exit valve spring 819. Piston core/exit check valve 807 provides a rigid substrate for the flexible piston 809 enabling high compression dispensing of treatment fluid. Its rib geometry fits inside of hollow piston shaft 805 to create concentric positioning of the core, yet allows fluid to pass up the shaft on the exit stroke. The flange geometry of piston core/exit check valve 807 seals against piston shaft 805 during the treatment fluid inlet stroke thereby preventing air intake through dispensing nozzle 821 and reducing or eliminating pump cavitation. This flange also provides a reaction structure for both the exit valve spring 819 and the piston return spring 811 through the stroke cycle. Flexible piston 809 provides a mechanical means of pressurizing the pump chamber 813 via displacement of actuation button 803. It displaces treatment fluid through the center core of piston shaft 805 on the dispensing stroke and provides negative pressure to draw fresh treatment fluid from the reservoir on the intake stroke. Dual "wiper" flanges 810 and 812 provide reliable sealing to pump chamber. Piston return spring 811 provides the return force necessary to drive the piston 809 through the intake stroke, thereby drawing fresh treatment fluid from the reservoir and recharging the main pump chamber 813. It also applies a sealing force to inlet ball check valve 817 against pump chamber 813 on the exit stroke. Main pump chamber 813 provides the main cylinder for pressurization during dispensing and intake strokes. It integrates the spherical mating/sealing surface for the inlet check valve 817, provides inlet tube 815 retention geometry, and integrates precision friction fit for upper pump chamber component 829. Inlet tube 815 transports treatment fluid from the reservoir into the main pump chamber 813 and attaches to main pump chamber 813 via precision friction slip fit. Inlet ball check valve 817 provides a means of sealing the inlet port during the dispensing stroke and thereby stops treatment fluid backflow into the reservoir. Exit valve spring 819 creates a force balance between exit check valve 807 and treatment fluid contained in the piston chamber 813. When actuation button 803 is depressed, exit valve spring 819 compresses, unseating the exit check valve 807 to allow pressurized fluid to exit the chamber 813. Spring force is overcome by piston return spring 811 to provide a means of sealing the pump chamber 813 during the treatment fluid inlet stroke, thereby preventing air intake through dispensing nozzle 821 and reducing or eliminating pump cavitation. Dispensing nozzle 821 provides a calibrated orifice through which a metered dosage of cleanser can exit the dispenser. It can be tuned to provide greater dosage velocity or wider dose distribution. The nozzle is affixed to the actuation button 803 via precise friction fit, sonic weld or chemical bond. Lower housing/reservoir 823 provides a means via internal rib geometry 837, 839, and 841, for enclosing, retaining and protecting the pump assembly and actuation components. It secures actuation button 821 to upper housing 801 via interlocking part geometry, secures location of the pump via rib geometry which has mating interface to pump geometry, and provides external rib geometry for tactile grip and/or purchase. As with the upper housing, the lower housing 823 provides for zone to over-mold soft touch elastomer material for additional tactile feedback and provides the balance of half the reservoir capacity for fluid to be dispensed. Additionally, it houses the main fill port 825 for refillable dispensers and incorporates geometry for retaining a neck lanyard. It can be secured to upper housing 801 via friction fit, sonic weld, chemical bond or mechanical fastener. Reservoir fill lid 843 is a soft, elastomeric component that encloses and seals the main fluid reservoir in lower housing 823 and is easily released for refilling by ergonomic tab feature at its top edge. It includes a "snap-fit" seal to lower housing 823 to prevent treatment fluid leakage. Pump assembly retention ring 827 retains the pump assembly in place between main housing halves. It is maintained in proper position by the rectangular box of rib geometry 837 and provides a seal between the treatment fluid reservoir and the actuation button cavity. Finally, upper pump chamber 829 retains the internal pump components in main pump chamber 813 via precision friction fit, chemical bond or sonic weld. It provides a precise, sealed bearing surface for piston shaft 805 and a reaction bearing surface for exit valve spring 819. FIG. 32 provides a view of the assembled pump mechanism properly positioned within the lower housing 823 alongside a cross-sectional view of the assembled mechanism.

Figure 33:
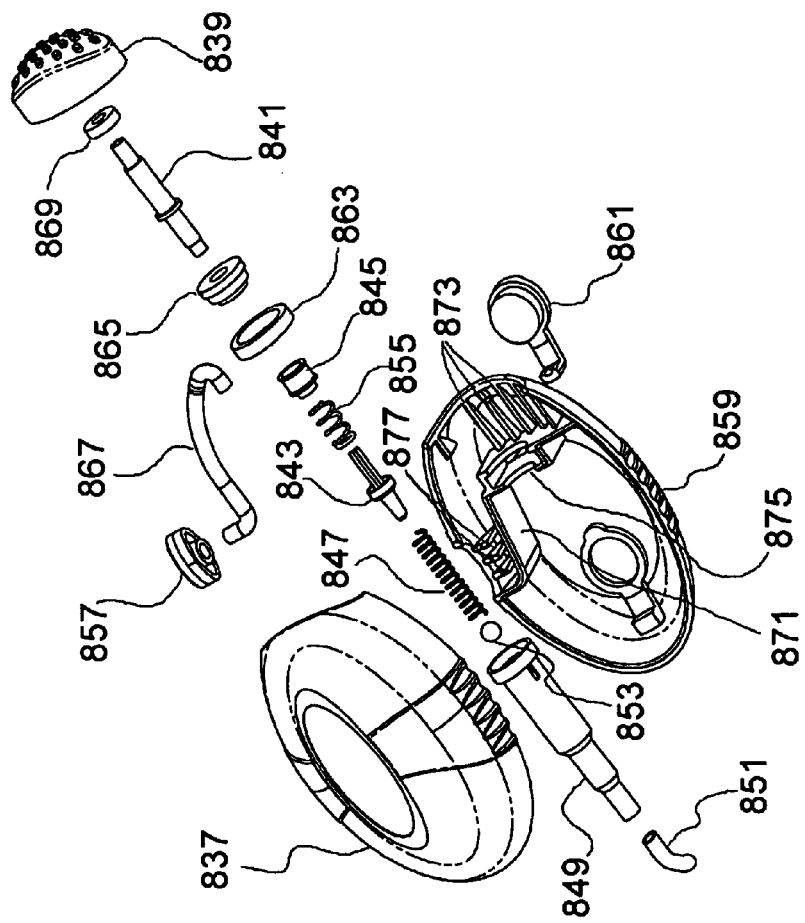
FIG. 33 is an exploded diagram of a second version of a neck-worn dispenser.

FIG. 33 is an exploded diagram of second version of the neck-worn dispenser featuring dispensing from a side-mounted nozzle 857. The parts layout and parts functions are the same as those of the first version shown in FIG. 31 with the exception of the side-mounted dispensing nozzle 857, dispensing nozzle tubing 867, dispensing tubing seal ring 869, partition rib 871, and ribs 877. The dispensing nozzle tubing 867 provides a means of routing exiting fluid from the center of the actuation button 839 to the side of the dispenser assembly. The tubing is flexible and includes slack to allow for actuation button stroke without binding. Dispensing tubing seal ring 869 provides a means of sealing and retaining the dispensing nozzle tubing 867. Partition rib 871 creates a space for the insertion of the dispensing nozzle 857 and ribs 877 support the dispensing nozzle 857. The following table identifies the remaining parts in FIG. 33.

| Part Number | Identity |
|---|---|
| 837 | Upper housing |
| 839 | Actuation button |
| 841 | Piston shaft |
| 843 | Piston core/exit check valve |
| 845 | Flexible piston |
| 847 | Piston return spring |
| 849 | Main pump chamber |
| 851 | Inlet tube |
| 853 | Inlet ball check valve |
| 855 | Exit valve spring |
| 859 | Lower housing/reservoir |
| 861 | Reservoir fill lid |
| 863 | Pump assembly retention ring |
| 865 | Upper pump chamber |

Figure 34:
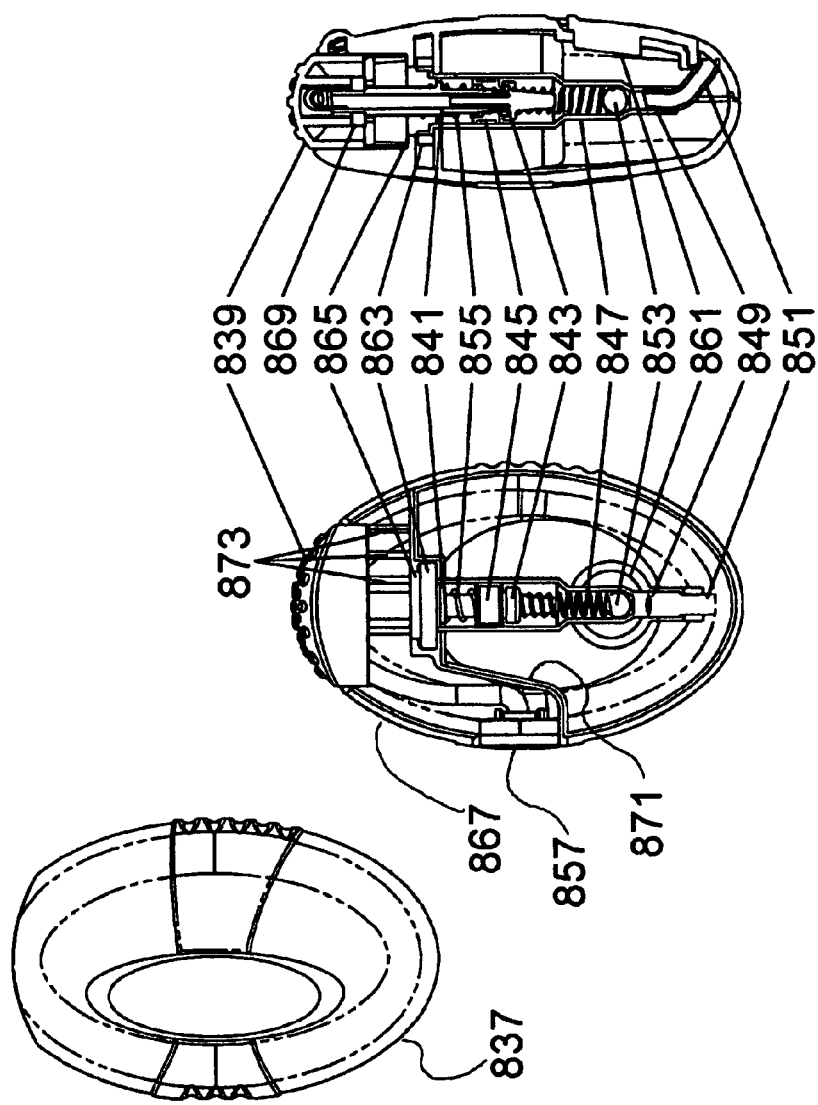
FIG. 34 is an assembled and cross-sectional view of the second version of a neck-worn dispenser.

FIG. 34 provides a view of the assembled pump mechanism of FIG. 33 properly positioned within the lower housing 859 alongside a cross-sectional view of the assembled mechanism.

Figure 35:
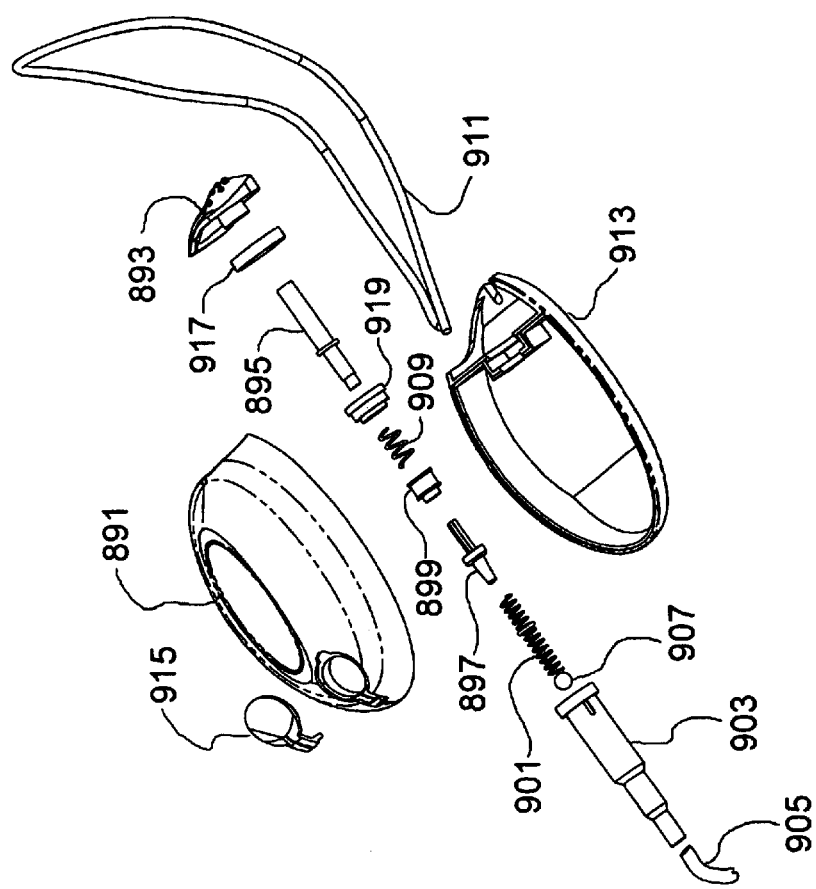
FIG. 35 is an exploded diagram of a third version of a neck-worn dispenser.
Figure 36:
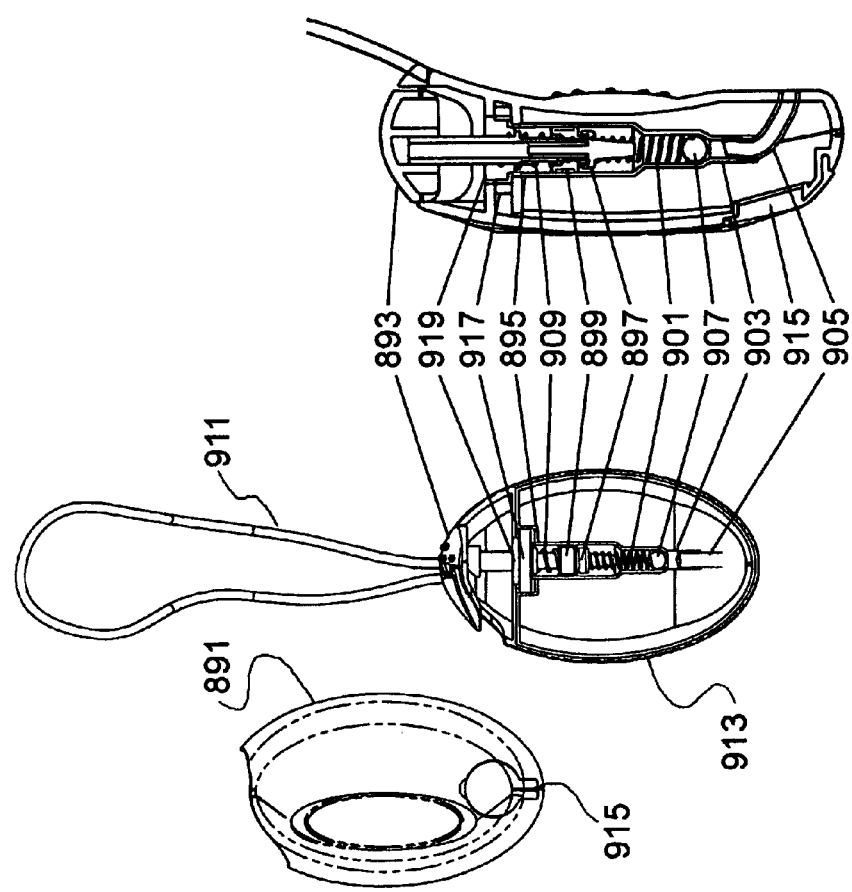
FIG. 36 is an assembled and cross-sectional view of the third version of a neck-worn dispenser.

FIG. 35 is an exploded diagram of third version of the neck-worn dispenser featuring dispensing from an end-mounted nozzle/button assembly 893, that is conformal with the shape of the dispenser. The parts layout and parts functions are the same as those of the first version shown in FIG. 31 with the exception of reduced ribbing in the housing, display of an attached lanyard 911, the nozzle/button assembly 893, and the presence of the refill lid 915 in the upper housing 891. The following table identifies the remaining parts in FIG. 33.

| Part Number | Identity |
|---|---|
| 891 | Upper housing |
| 893 | Nozzle/actuation button |
| 895 | Piston shaft |
| 897 | Piston core/exit check valve |
| 899 | Flexible piston |
| 901 | Piston return spring |
| 903 | Main pump chamber |
| 905 | Inlet tube |
| 907 | Inlet ball check valve |
| 909 | Exit valve spring |
| 913 | Lower housing/reservoir |
| 915 | Reservoir fill lid |

-continued

| Part Number | Identity |
| --- | --- |
| 917 | Pump assembly retention ring |
| 919 | Upper pump chamber |

Figure 37A:
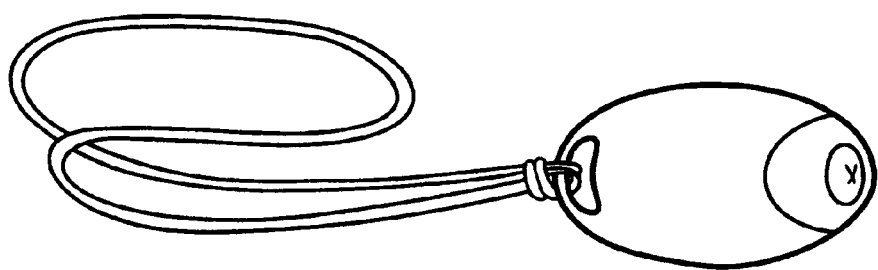
FIG. 37*a* is an pictorial diagram of a fourth version of a neck-worn dispenser.
Figure 37B:
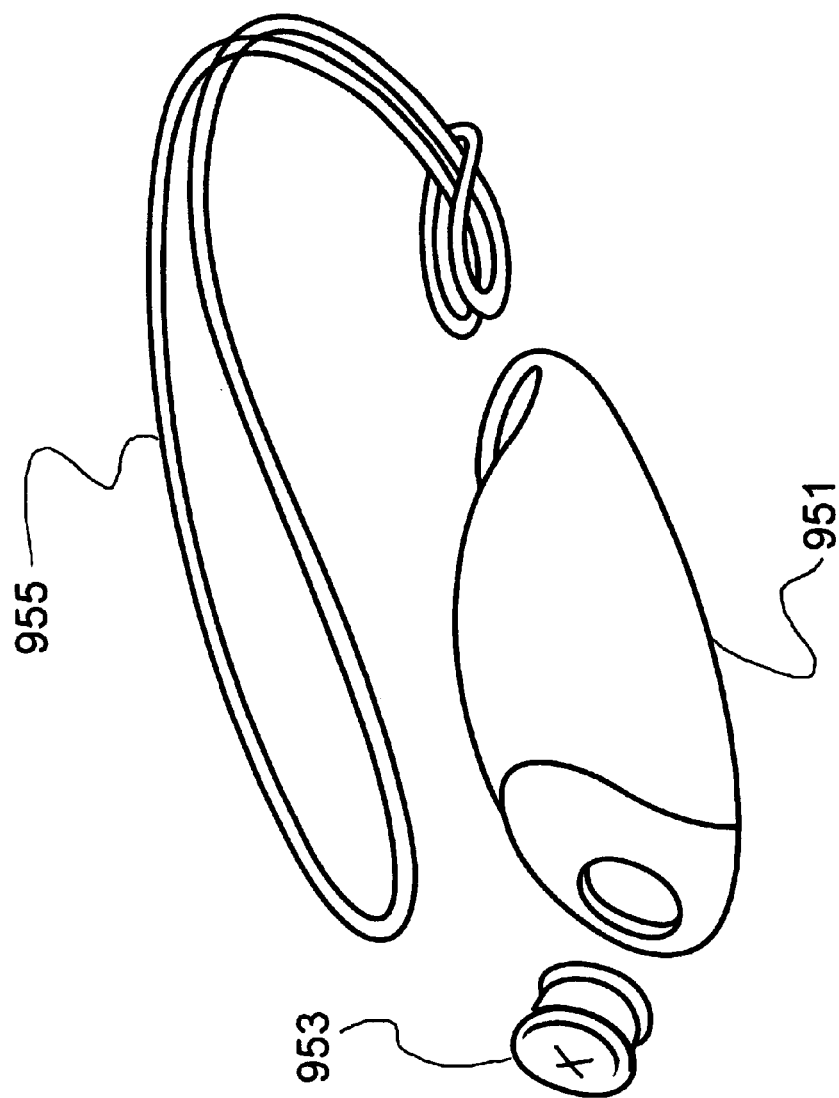
FIG. 37*b* is an exploded diagram of the fourth version of a neck-worn dispenser.

FIG. 37a is a pictorial view of a fourth version of the neck-worn dispenser. The corresponding exploded diagram is provided in FIG. 37b. Shown is a snap-fit, diphragm or self-sealing valve 953, a flexible molded reservoir body 951 with aperture 957 for retention of self-sealing valve 953, and an attachable lanyard 955. The reservoir 951 is constructed of a soft, flexible polymeric material, such as low density polyethylene (LDPE), such that a force can be applied by thumb or fore fingers on it upper surface to create a positive pressure on the treatment fluid contained within. The reservoir also contains molded-in details to retain one end of the neck lanyard 955. The diaphragm valve 953 is constructed of a soft, polymeric material that is "tuned" to deform under pressure from the treatment fluid. Once deformed, small slits in the diaphragm surface enable treatment fluid to be dispensed into the palm or onto the fingers of the non-actuating hand. The diaphragm valve has enough material rigidity to allow air to travel back in to replace the displaced hand treatment fluid, but not allow the fluid in the reservoir to escape unless a sufficient positive pressure is applied to the reservoir. Self-sealing, diaphragm valves will be discussed at length below in the context of disposable dispensers.

Figures 38A, 38B:
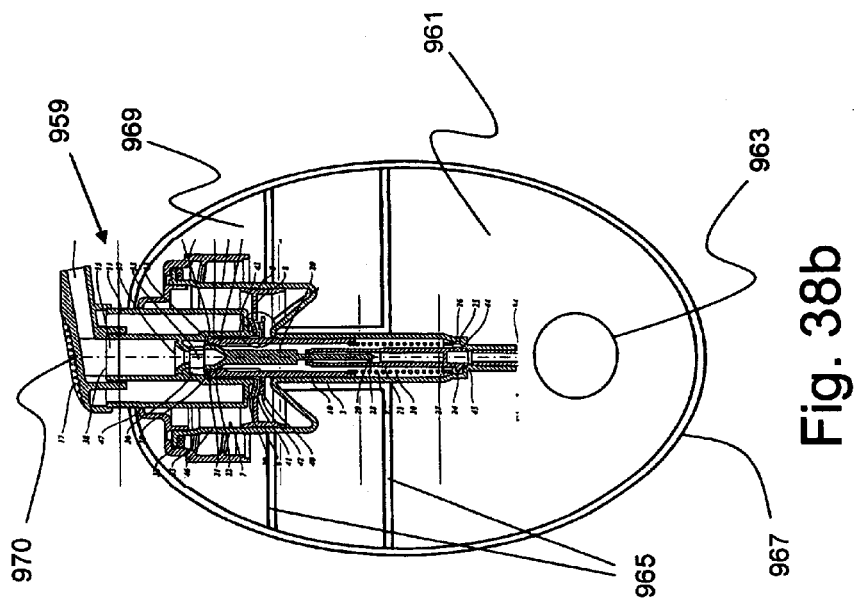
FIG. 38*a* is a cross-sectional view of a prior art foam dispensing mechanism.
FIG. 38*b* is a cross-sectional view of a neck-worn dispenser incorporating the mechanism of FIG. 38*a*.

FIG. 38 dipicts a foam generating mechanism and its employment in the present invention. FIG. 38a is a cross-sectional diagram of the mechanism disclosed in U.S. Pat. No. 6,053,364 to van der Heijden. This patent is hereby incorporated herein by reference thereto and details of the device operation are found in the text of this patent. The disclosed mechanism enables the dispensing of an air-liquid mixture in the form of foam. By providing for more efficient application of the hand treatment to the skin, foam conserves the amount of treatment material used. FIG. 38b depicts the use of the foam-generating mechanism 959 in a neck-worn embodiment of the present invention. Depicted is the lower half of a housing reservoir 967 with a rib geometry 965 that holds the mechanism 959 in place and partitions the reservoir into a treatment fluid containing space 961 and an air-filled space 969. The treatment fluid space is refillable through aperture 963. Air filled space 969 is in further fluid communication with air external to the dispenser housing by either loose sealing of the housing around the actuation end 970 of the foaming mechanism or by a small aperture (not shown) in the top region of the housing. This permits the appropriate air and fluid intake areas of the mechanism to be in fluid communication with air and treatment fluid volumes, respectively, as is detailed in the patent to van der Heijden. The mechanism disclosed by van der Heijden can be adapted to facilitate its use in the present invention and diminish its manufacturing cost. As an example, in miniaturization of the mechanism, the diameter of passageways relative to the overall size of the mechanism can be made proportionally larger than those of the full size device.

Slit-Based Membrane Valve Embodiments

Figure 39C:
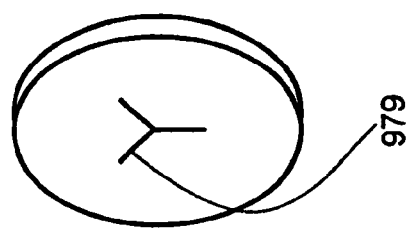
FIG. 39*c* is a pictorial diagram of a tricuspid-type diaphragm valve.
Figure 39B:
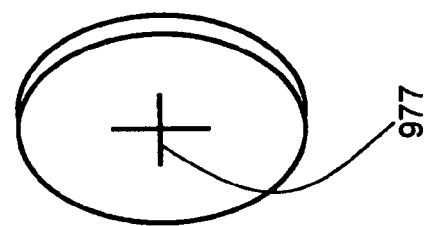
FIG. 39*b* is a pictorial diagram of a diaphragm valve have cross slits.
Figure 39A:
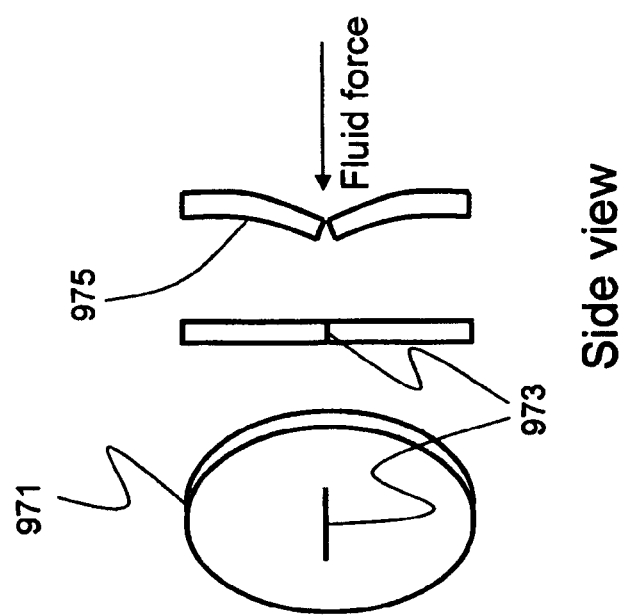
FIG. 39*a* is a pictorial and side view diagram of a single slit diaphragm valve.

FIGS. 40 through 47 depict various slit-based membrane valve embodiments of the invention. These embodiments are characterized by use of the aforementioned self-sealing diaphragm valves. As shown in FIGS. 40 though 47, the membrane valve is located in a region of the dispenser surface exhibiting a smooth substantially outwardly curved profile that immediately surrounds the valve. FIGS. 39a through 39c depict the basic geometry of self-sealing diaphragm valves. In FIG. 39a a simple disc membrane 971 of flexible polymeric material is shown with a central slit 973. The thickness and construction of this diaphragm valve along with the nature of the polymer employed provide sufficient stiffness that inadvertent fluid leakage will not occur. As shown in the side view of the diaphragm, when sufficient fluid force is applied to one side of the diaphragm, the flaps of the slit open to release fluid, but otherwise close to provide a seal. Low density polyethylene (LDPE) is one of a number of good candidate materials for this type of valve. Other slit geometries are feasible such as the cross 977 of FIG. 39b and the tri-slit 979 of FIG. 39c which resembles the tricuspid valve of the human heart. Variations in the cross-sectional thickness of the diaphragm valve offer potential advantages such as rigidity of the valve perimeter for mounting into the reservoir.

Figure 41:
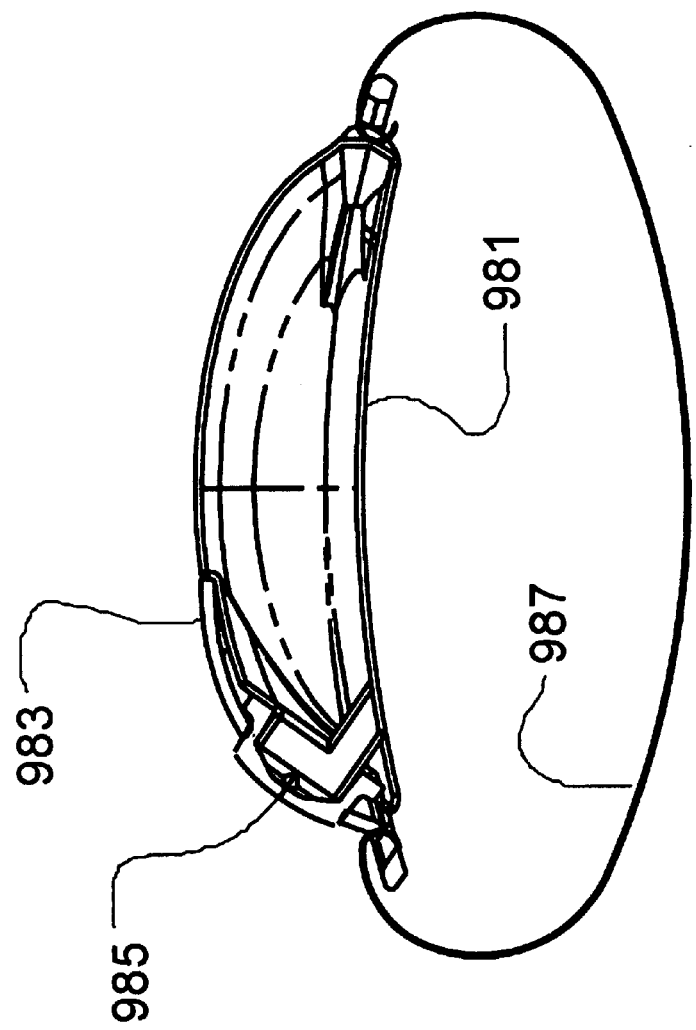
FIG. 41 is a cross-sectional diagram of the device of FIG. 40.

A first version of the slit-based membrane valve type dispenser is shown in FIG. 40. A self-sealing diaphragm valve of the type just described is part of the diaphragm valve assembly 985 is constructed of a soft, polymeric material that is "tuned" to deform under pressure from the treatment fluid. Once deformed, small slits in the diaphragm surface enable treatment fluid to dispense into palm or fingers of the actuating hand. Again, the diaphragm has enough material rigidity to allow air to travel back in to replace the displaced cleanser, but not allow the treatment fluid in the reservoir to escape unless a positive pressure is applied to the flexible reservoir 981. The valve assembly retainer 983 is a rigid polymeric component that retains the flexible diaphragm valve 985 in its service position. It also enables attachment of one end of the retention of the wrist strap 987. The wrist strap 987 is a flexible material (such as non-woven polyethylene) with re-usable adhesive on at least one side such that the strap could be placed over hand and around several sizes of wrists and be secured for its service cycle, and then disposed. FIG. 41 is a cross-sectional diagram of this version of the invention showing captivation of the diaphragm valve assembly 985 by the valve assembly retainer 983.

Figure 42:
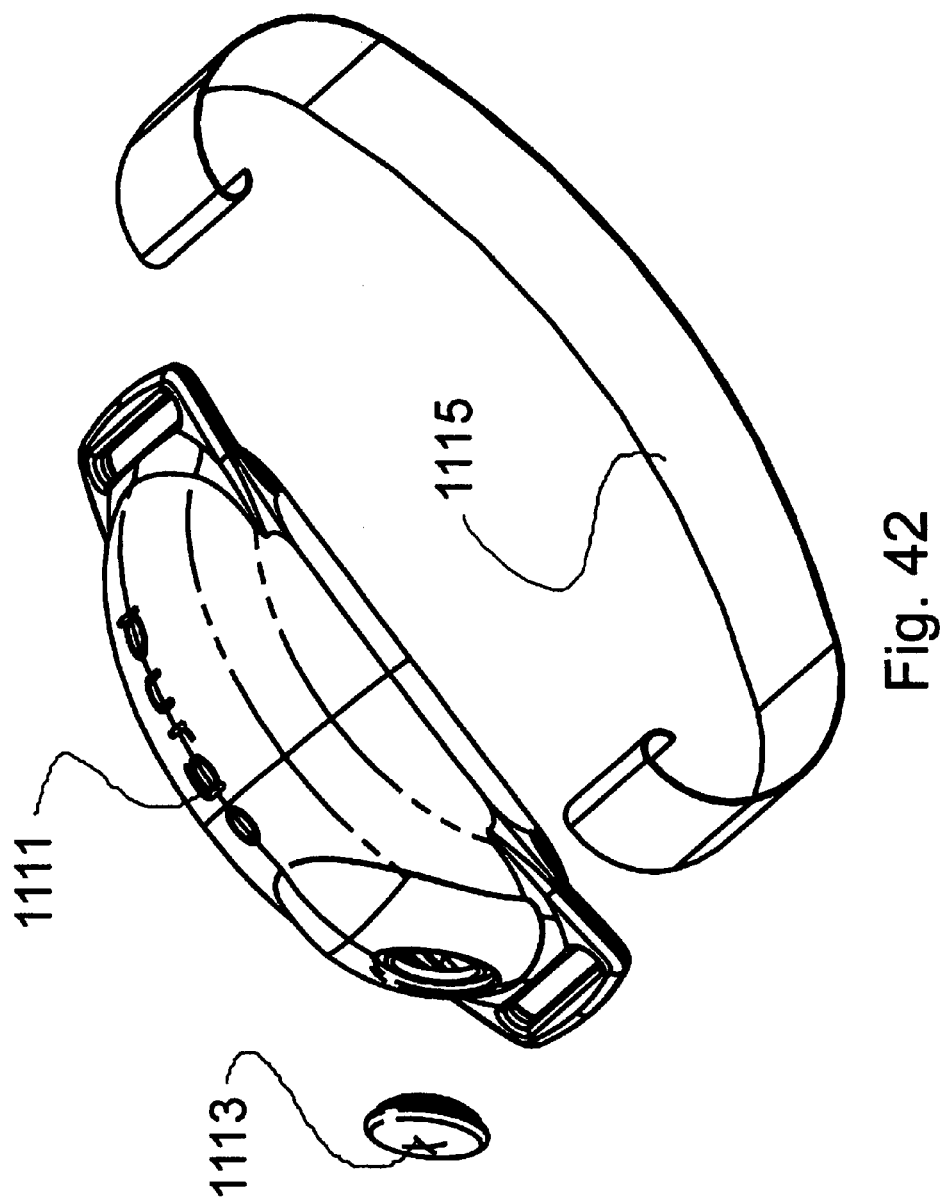
FIG. 42 is an exploded diagram of a second version of a slit-based membrane valve embodiment of the invention in which the valve snap-fits into the reservoir.
Figure 43:
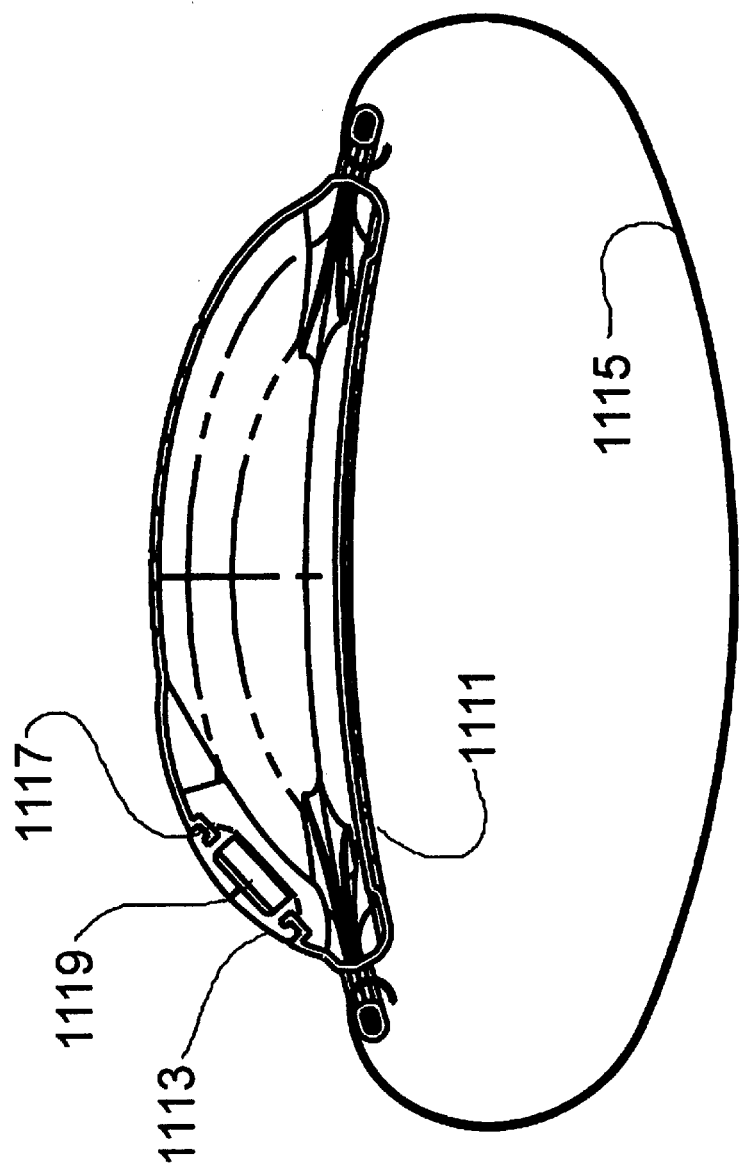
FIG. 43 is a cross-sectional diagram of the device of FIG 42.

FIG. 42 is an exploded diagram of a second version of the slit-based membrane valve type dispenser that uses a valve 1113 that snap-fits into the reservoir 1111. This is better understood with reference to the cross-sectional diagram of FIG. 43. The flange 1119 on the valve 1113 snap fits around a corresponding shaped flange 1117 in the aperture of reservoir 1111. Also shown is the wrist strap 1115.

Figure 44:
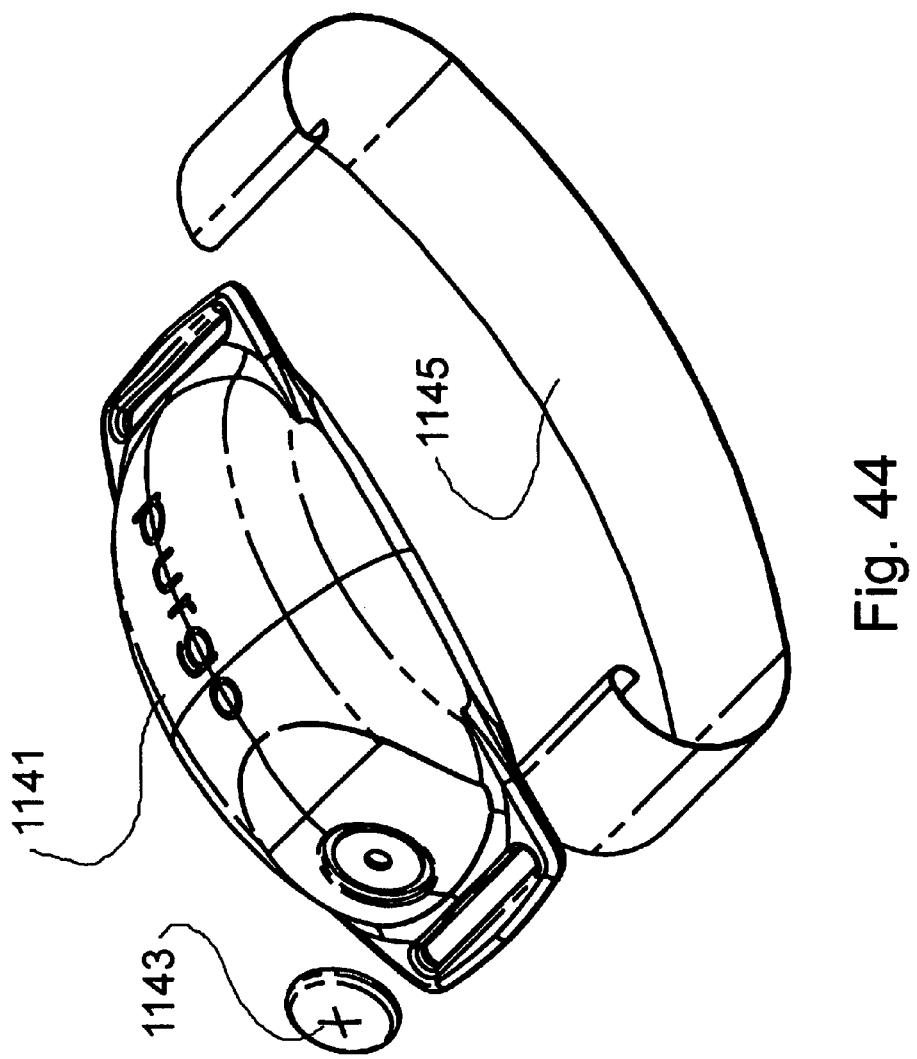
FIG. 44 is an exploded diagram of a slit-based membrane vain embodiment of the invention exhibiting an insert-molded valve.
Figure 45:
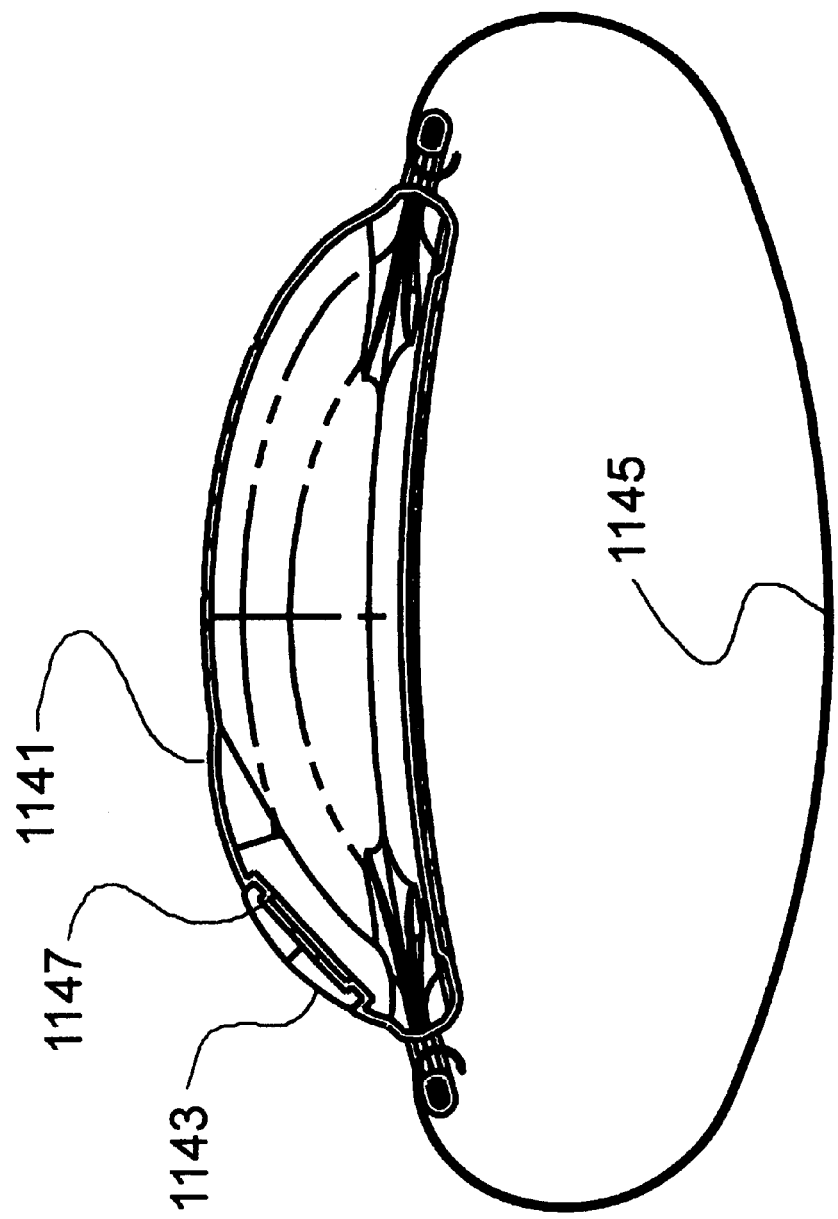
FIG. 45 is a cross-sectional diagram of the device of FIG. 44.

FIG. 44 is an exploded diagram of a third version of the slit-based membrane valve type dispenser that makes use of a diaphragm valve 1143 that is integrally- or insert-molded to the reservoir 1141. Wrist strap 1145 is depicted also. In the cross-sectional diagram of FIG. 45, the valve 1143 is shown molded to the valve seating surface 1147 of the reservoir 1141.

Figure 46:
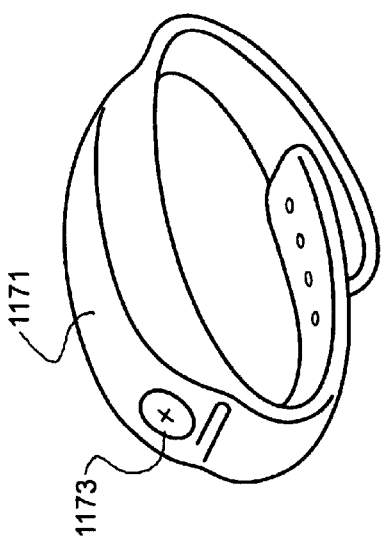
FIG. 46 is a pictorial diagram of a slit-based membrane valve embodiment of the invention in which the wristband is one piece with the reservoir.
Figure 47:
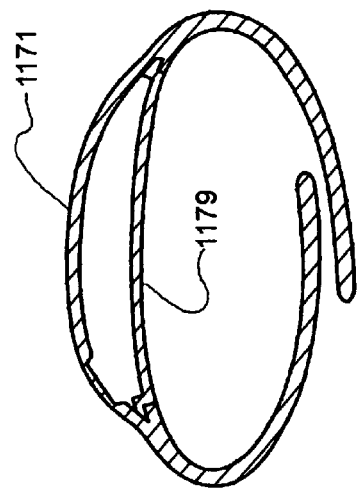
FIG. 47 is a cross-sectional diagram of the device of FIG. 46.

FIG. 46 is a pictorial diagram of a fourth version of the slit-based membrane valve type dispenser in which the valve 1173 is integral to the upper portion 1171 of the reservoir. The upper portion of the reservoir consists of one integrally molded component from an elastomeric type material. The component geometry includes the diaphragm valve 1173 and the wrist strap. The upper portion 1171 of the reservoir 1171 is bonded to the lower portion 1179 of the reservoir. Here again LDPE plastic is an ideal candidate construction material.

Depending upon the compounding of the specific treatment fluid to be dispensed by the present invention, various biodegradable plastics can be employed in disposable embodiments of the invention. The table below provides examples of various categories of candidate biodegradable plastics.

| Biodegradable Plastics | | | |
|---|---|---|---|
| Category | Generic Name | Trade Name | Producer |
| Biopolymer | Poly 3-hydroxybutyrate | Biogreen | Mitsubishi Gas Chemicals |
| Synthetic Polymer | Polybutylenesuccinate | Bionelle 1000 | Showa Highpolymer |
| | Polybutylenesuccinate/adipate | Bionelle 3000 | Showa Highpolymer |
| | | EnPol 4000 | Ire Chemical |
| | Polybutylenesuccinate/carbonate | Iupec | Mitsubishi Gas Chemicals |
| | Polybutylenesuccinate/terephthalate | Biomax | Dupont |
| | Polybutyleneadipate/terephthalate | Ecoflex | BASF |
| | Polytetramethyleneadipate/terephthalate | EasterBio | Eastman Chemicals |
| | Polybutyleneadipate/terephthalate | EnPol 8000 | Ire Chemical |
| | Polycaprolactone | CelGreen PH | Daicel Chemical |
| | | TONE | Dow Chemical |
| | Polyethylensuccinate/adipate | Lunare SE | Nippon Shokubai |
| | Polylactic Acid | NatureWorks | Cargill Dow |
| | | LACEA | Mitsui Chemicals |
| | Polyvinyl Alcohol | Poval | Kuraray |
| | | Gosenol | Nippon Synthetic Chemical |
| | | Dolon VA | Aicello Chemical |
| Modified Natural Polymer | Modified Starch | Cornpol | Japan Cornstarch |
| | Starch-based Synthetic Polymer | Placorn | Nihon Shokuhin Kako |
| | | Mater-Bi | Chemitech |
| | Cellulose Acetate | CelGreen PCA | Daicel Chemical |
| | | Unknown | Teijin |
| | Chitosan/Cellulose/Starch | Dolon CC | Aicello Kagaku |

The invention claimed is:

1. A body-worn treatment dispenser comprising:
  a) a dispensing reservoir containing treatment material, for containment and dispensing of said treatment material, said dispensing reservoir exhibiting an interior volume formed by upper and lower portions of said reservoir, said upper portion having an exterior surface,
  b) a slit-based diaphragm valve having flaps and exhibiting an interior surface in fluid communication with said interior volume of said dispensing reservoir and an exterior surface with a shape that is substantially convex through which said treatment material is dispensed, said exterior surface of said slit-based diaphragm valve being contiguous with said exterior surface of said upper portion of said reservoir, said slit-based diaphragm valve of a different thickness than said upper portion of said reservoir,
  c) body attachment means comprising a flexible wristband further comprising elongation or extension of said upper portion at substantially opposing positions about said interior volume, manual deformation of a flexible portion of said reservoir providing pressure on said treatment material contained in said reservoir and thereby an said diaphragm valve so as to cause dispensing of said treatment material through said flaps while said dispenser is being worn.

2. A body-worn treatment dispenser as recited in claim 1 wherein said reservoir is constructed of low density deformable polymer.

3. A body-worn treatment dispenser as recited in claim 1 wherein said reservoir is constructed of elastomeric polymer.

4. A body-worn treatment dispenser as recited in claim 1 wherein at least a portion of said dispenser is constructed from biodegradable polymer.

5. A body-worn treatment dispenser as recited in claim 4 wherein at least a portion of said dispenser is constructed from biodegradable polymer selected from the group comprising: poly 3-hydroxybutyrate, polybutylenesuccinate, polybutylenesuccinate/adipate, polybutytenesuccinate/carbonate, polybutylenesuccinate/terephthalate, polybutyleneadipate/terephthalate, polytetramethyleneadipate/terephthalate, polycaprolactone, polyethylenesuccinatel/adipate, polylactic acid, polyvinyl alcohol, modified starch, starch-based synthetic polymer, cellulose acetate, chitosan/cellulose/starch.

6. A method of dispensing an amount of treatment material, said method comprising the steps of:
  a) providing a portable dispenser comprising:
    i) a dispensing reservoir containing treatment material, for containment and dispensing of said treatment material, said dispensing reservoir exhibiting an interior volume formed by upper and lower portions of said reservoir, said upper portion having an exterior surface,
    ii) a slit-based diaphragm valve having flaps and exhibiting an interior surface in fluid communication with said interior volume of said dispensing reservoir and an exterior surface with a shape that is substantially convex through which said treatment material is dispensed, said exterior surface of said slit-based diaphragm valve being contiguous with said exterior surface of said upper portion of said reservoir, said slit-based diaphragm valve of a different thickness than said upper portion of said reservoir, and
    iii) body attachment means comprising a flexible wristband further comprising elongation or extension of said upper portion at substantially opposing positions about said interior volume b) removably attaching said dispenser to a person, c) forcing said treatment material immediately from said reservoir through said flaps by squeezing said reservoir with one hand of said person, d) dispensing an amount of said treatment material into said one hand while said dispenser is worn by said person.

* * * * *